(12) United States Patent
Song et al.

(10) Patent No.: US 11,600,363 B2
(45) Date of Patent: Mar. 7, 2023

(54) PTF-BASED METHOD FOR PREDICTING TARGET SOIL PROPERTY AND CONTENT

(71) Applicant: INSTITUTE OF SOIL SCIENCE, CHINESE ACADEMY OF SCIENCES, Jiangsu (CN)

(72) Inventors: Xiaodong Song, Jiangsu (CN); Ganlin Zhang, Jiangsu (CN); Decheng Li, Jiangsu (CN); Feng Liu, Jiangsu (CN); Huayong Wu, Jiangsu (CN); Fei Yang, Jiangsu (CN); Jinling Yang, Jiangsu (CN); Yuguo Zhao, Jiangsu (CN)

(73) Assignee: INSTITUTE OF SOIL SCIENCE, CHINESE ACADEMY OF SCIENCES, Jiangsu (CN)

( * ) Notice: Subject to any disclaimer, the term of this patent is extended or adjusted under 35 U.S.C. 154(b) by 0 days.

(21) Appl. No.: 17/577,006

(22) Filed: Jan. 16, 2022

(65) Prior Publication Data

US 2022/0189588 A1 Jun. 16, 2022

Related U.S. Application Data

(63) Continuation of application No. PCT/CN2020/093267, filed on May 29, 2020.

(30) Foreign Application Priority Data

Mar. 19, 2020 (CN) .......................... 202010195020.4

(51) Int. Cl.
G16C 20/00 (2019.01)
G16C 20/30 (2019.01)
G06N 5/022 (2023.01)

(52) U.S. Cl.
CPC ............. *G16C 20/30* (2019.02); *G06N 5/022* (2013.01)

(58) Field of Classification Search
CPC ................................. G06N 5/022; G16C 20/30
(Continued)

(56) References Cited

U.S. PATENT DOCUMENTS

| | | | |
|---|---|---|---|
| 2018/0049364 A1* | 2/2018 | Campisi-Pinto | G06F 17/40 |
| 2018/0172659 A1* | 6/2018 | Visser | G01N 33/24 |
| 2019/0050948 A1* | 2/2019 | Perry | G06Q 10/04 |

FOREIGN PATENT DOCUMENTS

| | | |
|---|---|---|
| CN | 106980603 | 7/2017 |
| CN | 106980750 | 7/2017 |
| CN | 108764527 | 11/2018 |

OTHER PUBLICATIONS

Predicting the soil properties in the tropics (Year: 2011).*
(Continued)

*Primary Examiner* — Tsu-Chang Lee
(74) *Attorney, Agent, or Firm* — JCIPRNET

(57) ABSTRACT

Provided is a pedo-transfer function (PTF)-based method for predicting a target soil property. Based on the collection of a multi-source soil dataset and environmental variables, a dataset containing all measured information is divided. Second-level regions are obtained by zoning according to the spatial variation in soil properties. An optimal independent variable set of PTFs in different regions is obtained by screening. Then, linear fitting and nonlinear fitting of the PTFs are performed for different zones separately. By comparing the accuracy of different functions between different zones, optimal PTFs oriented toward sampling sites are selected, so as to build a database including soil sampling sites. Further, regional independent variable layers are constructed by means of machine learning, to establish region-oriented PTFs; and a spatial distribution map of the target soil property and content for a target region is produced.

10 Claims, 9 Drawing Sheets

(58) Field of Classification Search
USPC .......................................................... 706/12
See application file for complete search history.

(56) References Cited

OTHER PUBLICATIONS

Rasmussen, et al., "Beyond clay: toward an improved set of variables for predicting soil organic matter content", Biogeochemistry (2018) 137:297-306 (Year: 2018).*
"International Search Report (Form PCT/ISA/210) of PCT/CN2020/093267," dated Sep. 1, 2020, with English translation thereof, pp. 1-4.
"Written Opinion of the International Searching Authority (Form PCT/ISA/237) of PCT/CN2020/093267," dated Sep. 1, 2020, with English translation thereof, pp. 1-10.

* cited by examiner

|  | S_1 | S_2 | S_3 | S_4 | S_5 |
|---|---|---|---|---|---|
| Sampling site 1 | 12.2 | 6.4 | 65 | 100.5 |  |
| Sampling site 2 | 5.3 |  | 20 | 65.7 |  |
| Sampling site 3 | 8.6 | 9.2 | 40 | 84.5 | 32.4 |
| Sampling site 4 | 6.4 | 6.8 | 32 | 98.5 | 65.2 |
| Sampling site 5 | 6.3 | 6.7 | 68 | 112.5 | 12.4 |
| Sampling site 6 |  | 6.9 | 87 | 6.5 |  |

PTF-BASED METHOD FOR PREDICTING TARGET SOIL PROPERTY AND CONTENT

CROSS-REFERENCE TO RELATED APPLICATION

This application is a continuation of international application of PCT application serial no. PCT/CN2020/093267 filed on May 29, 2020, which claims the priority benefits of China application no. 202010195020.4, filed on Mar. 19, 2020. The entirety of each of the above mentioned patent applications is hereby incorporated by reference herein and made a part of this specification.

BACKGROUND

Technical Field

The present disclosure relates to a pedo-transfer function (PTF)-based method for predicting a target soil property and content, and belongs to the technical filed of soil.

Description of Related Art

As an important carrier in the human living environment, soil has a close relationship with the social and economic development. Since the 20th century, the rapid development of global industrialization leads to a dramatic increase in the content of heavy metals in soil, and especially, the soil in industrial areas and around various mining areas has very high content of heavy metals, seriously affecting the stability of the ecosystem, and attracting the attention of relevant departments and the majority of people around the world. Therefore, this issue is a globally recognized hot topic. It is suggested to use more ecological and environmentally friendly organic fertilizer for the development of sustainable ecological agriculture. However, cow and pig manure, which are widely applied in current agricultural production, produce sugars, phenols, organic acids, and other compounds in the soil, easily causing chelation or complexation of soil copper and bringing potential environmental pollution. Soil phosphorus is one of the main macroelements for plant growth. However, according to relevant statistics, the soil phosphorus content in agroecosystems is lower than the demand of plant growth, which has led to a rapid increase in the phosphate fertilizers consumption in China over the past three decades. Irrational overuse of the phosphate fertilizers directly leads to the accumulation of large amounts of phosphate in the soil, thus significantly affecting the utilization (about 10%-20%) of the phosphate fertilizers applied in season and causing the loss and waste of the phosphate fertilizer resource. The accumulation of large amounts of phosphorus in agricultural soil may indirectly cause serious environmental problems, such as the eutrophication of water body caused by the migration of phosphorus with the water body. Therefore, it is of great significance to periodically monitor the soil properties and content.

Soil databases created by different application departments generally cover only the basic soil physicochemical properties, but rarely involve content data of trace elements and heavy metals in the soil. For example, the WoSIS soil database created by Wageningen University and Harmonized World Soil Database v 1.2 (HWSD) created by the Food and Agriculture Organization of the United Nations only include basic physicochemical properties such as soil organic matters, pH, texture, nitrogen, phosphorus, potassium, etc.

Domestic and foreign relevant technical departments, companies and scholars have proposed a series of chemical measurement methods for the soil properties and contents. For example, feasible methods for measuring the available copper content in soil include: using an atomic absorption spectrometer, a DTPA-TEA extraction method, using an atomic absorption spectrophotometer, etc.; and feasible methods for measuring total phosphorus content in soil include: a high-temperature burning and acid extraction method, a strong acid boiling method, an alkali fusion method, and using a continuous flow analyzer, etc. A conventional method of acquiring information about the soil properties and contents includes field sample collection and laboratory chemical analysis. This method has high accuracy but is laborious, and thus it is impossible to obtain the spatial distribution information of soil properties at the regional scales through this method. In recent years, some scholars try to use spectroscopy (e.g., visible and near infrared reflectance (VNIR) spectra) to deduce soil properties. Iron oxides and organic matters in soil have certain adsorption effect on the soil heavy metals and assume certain absorption characteristics on the spectral curve, and thus the content of soil heavy metals can be indirectly predicted. Based on the response characteristics of soil elements to the spectrum, a prediction model (for example, a partial least squares regression model) of total soil phosphorus and different spectral indicators can also be constructed. This kind of methods have significant advantages such as high efficiency, non-destructive effect, and high speed; and has a high potential for application in rapid detection of soil constituents. However, such methods have a certain measurement error in specific application, and the measurement errors vary a lot between different study areas and different operators.

However, different soil survey departments have different demands in practice. Limited by budgetary expenditures, these departments are unable to measure all soil physicochemical indicators, but can only measure some soil physicochemical properties relevant to specific needs, for example, a soil microbial survey, an engineering soil survey, and the like. Therefore, some of the soil surveys collect a number of soil samples, whereas the heavy metal content is not always analyzed. Since most of these legacy soil samples have not been archived, it is impossible to fill gaps in missing soil data (e.g. nitrogen, phosphorus and potassium contents in the soil) through laboratory analysis. Especially, when agriculture and ecology departments integrate multi-source soil data for soil quality and fertility evaluation, they often find that key soil properties are missing at many soil sampling sites.

In view of the similar problem of lack of data in the database, technicians propose to use PTFs to add the missing soil data. Based on the correlation between soil physical and chemical properties, the PTF can update the missing data by constructing a prediction model for measured and unmeasured soil properties. Frequently used PTF models mainly include a statistical regression model, an artificial neural network, a physical experience model, and the like. The statistical regression model is widely adopted in practice due to the advantages of easy implementation, high prediction accuracy, and variable importance measurement.

With the rapid development of sensor technology, the geographic information system, the global positioning system and other technologies, departments such as geography, geology, meteorology, remote sensing, and land planning have produced a large number of spatial geographic information data, such as soil temperature, evapotranspiration, mean annual precipitation (MAP), mean annual temperature (MAT), mean annual sunshine, humidity index, land utilization, elevation, and other terrain attributes. From the perspective of pedogenesis, the soil evolution is mainly driven by a combination of five soil-forming factors: climate, topography, parent material, organisms, and time. The spatial variability of the soil physicochemical properties, namely, a soil-landscape model, may be simulated and predicted by using variables of soil-forming elements. Such technology has been widely applied in the field of digital soil mapping.

At present, the PTF-based prediction of the soil properties and contents has certain limitations in prediction and evaluation techniques, which specifically include:

(1) By a search through relevant technical literature, patents and reports, it is found that PTF-based techniques for predicting the soil properties are scarce, except soil bulk density and soil hydrological parameter. This could be attributed to the low correlation between some soil properties and other soil physicochemical properties. In addition, environmental variables related to soil-forming factors are rarely considered during the PTF construction. The data amount can directly affect the accuracy of the PTFs, particularly when there is a low correlation between the soil physicochemical properties, which requires a large amount of soil data for the model calibration. The lack of integration of environmental variables affects the accuracy of the PTFs in prediction of the soil properties and contents to a certain extent.

(2) Uncertainty should be considered in the practical application, which might be propagated from soil data, environmental variables, model training and model validation. Every mathematical statistical model may be characterized with uncertainty, which is also an important element that is lacked in the practical application of the PTFs. For example, the PTF based on the least square method is needed to determine the errors of input elements (the soil physicochemical properties) before evaluating the propagation of uncertainty involved in this linear model via a relevant prediction model.

(3) The acquired PTFs can only predict soil information at the sampling point scale, but cannot produce a soil map covering all the unvisited sites, which can provide essential soil information for the whole area rather than limited sampling sites and thus can benefit more application departments in practice. Because the input data of the conventional PTFs are soil physicochemical data analyzed in the laboratory, the fitted equations represent only the relationships between the measured soil properties. Furthermore, the accuracy of soil map covering the whole region is usually lower than that of soil observations obtained by laboratory analysis, and thus these PTFs cannot be directly applied in the legacy soil map for production of a spatial distribution map of the soil property.

The above-described shortcomings in the existing soil property prediction technology have affected the specific benefits in production and processing of soil information products by application departments related to biology, agronomy, and environment, thus causing economic losses to the national ecological planning and precision agriculture management to a certain extent.

SUMMARY

The technical problem to be solved by the present disclosure is to provide a PTF-based method for predicting a target soil property and content, which overcomes the shortcomings in the prior art by using a new design architecture, thus efficiently realizing accurate prediction of the target soil property and content and improving the working efficiency.

The present disclosure adopts the following technical solution to solve the foregoing technical problem: The present disclosure designs a PTF-based method for predicting a target soil property and content, which is used to realize prediction of the target soil property and content in a target region and includes the following steps:

Step A. selecting, based on existing soil data, sampling sites of which data values of corresponding preset soil physicochemical properties are non-null from the target region, and partitioning a first-level region with a smallest bounding polygon covering all the selected sampling sites, wherein the sampling sites are used as sampling sites corresponding to the first-level region, the preset soil physicochemical properties comprise a target soil property that is referred to as a soil dependent variable and is defined as the target soil property, and rest of the soil physicochemical properties that are used to form a soil independent variable set; and then, proceeding to Step B;

Step B. acquiring layers, covering the first-level region, of specified environmental variables related to the soil dependent variable; deriving, for the sampling sites corresponding to the first-level region, values from the specified environmental variables at the sampling sites, and adding the derived values to the soil independent variable set, to update the soil independent variable set; and then, proceeding to Step C;

Step C. deleting independent variables causing multicollinearity and independent variables of which the correlation with the soil dependent variable is less than a preset significant difference threshold, from the soil independent variable set, to update the soil independent variable set; and then, proceeding to Step D;

Step D. training, for the sampling sites corresponding to the first-level region, a linear relationship between the soil dependent variables and the soil independent variables in the soil independent variable set by using a stepwise multiple linear regression model based on a preset number of iterations; separately acquiring a temporary optimal independent variable set during each training iteration, and recording a selection number of each of temporary optimal independent variable sets; adopting, after completion of training for the preset number of iterations, a temporary optimal independent variable set which is most frequently screened as the optimal independent variable set corresponding to the first-level region; and then, proceeding to Step E;

Step E, acquiring layers of a soil region with preset properties that cover the first-level region, and extracting, for the sampling sites corresponding to the first-level region, soil zones with the preset properties where the sampling sites are located; analyzing and obtaining, based on the data values of the soil dependent variable at the sampling sites, difference results in the soil dependent variable between different soil zones; if none of the difference results are greater than the preset significant difference threshold, proceeding to Step G; merging, if there is a difference result greater than the preset significant difference threshold in the obtained difference results, the soil zones with the difference results not greater than the preset significant difference threshold, and partitioning second-level regions in combination with the soil zones that are not merged; acquiring, based on the sampling sites corresponding to the first-level region, sampling sites corresponding to the second-level regions; and then, proceeding to Step F;

Step F, acquiring, for each of the second-level regions, an optimal independent variable set corresponding to each of the second-level regions by using the method described in Step D, and then proceeding to Step G;

Step G, training, for the sampling sites corresponding to the first-level region, a linear regression model and a nonlinear regression model between the data values of the soil dependent variables and the data values of independent variables in the corresponding optimal independent variable set; and acquiring a coefficient of determination of the linear regression model and that of the nonlinear regression model, wherein the coefficient of determination of the linear regression model corresponding to the first-level region is R_OLS and the coefficient of determination of the nonlinear regression model corresponding to the first-level region is R_NLS; further, if there is no second-level region, then, proceeding to Step H; or if there are second-level regions, for the second-level regions, separately training a linear regression model and a nonlinear regression model between the data values of the soil dependent variables at the sampling sites and the data values of the independent variables in the corresponding optimal independent variable set, and acquiring the coefficient of determination of the linear regression model and that of the nonlinear regression model, thus acquiring coefficients of determination of linear regression models and nonlinear regression models corresponding to all the second-level regions, and further acquiring mean values of these coefficients of determination of the linear regression models and nonlinear regression models corresponding to all the second-level regions, which are termed R_OLS_mean and R_NLS_mean, respectively; and then, proceeding to Step H;

Step H, if there is no second-level region, proceeding to Step I;

if there are second-level regions, when R_OLS is greater than both R_OLS_mean and R_NLS_mean or R_NLS is greater than both R_OLS_mean and R_NLS_mean, proceeding to Step I; and when R_OLS_mean is greater than both R_OLS and R_NLS or R_NLS_mean is greater than both R_OLS and R_NLS, proceeding to Step M;

Step I, based on the sampling sites corresponding to the first-level region and the corresponding optimal independent variable set, and according to data values of soil physicochemical properties in the optimal independent variable set corresponding to the sampling sites, acquiring a prediction model based on all the specified environmental variables in Step B for each soil physicochemical property in the optimal independent variable set; acquiring spatial distribution prediction layers of the soil physicochemical properties in the optimal independent variable set corresponding to the first-level region according to the layers of the specified environmental variables in Step B;

and then, proceeding to Step J;

Step J, merging the spatial distribution prediction layers of the soil physicochemical properties and the environmental variables in the optimal independent variable set corresponding to the first-level region, to form an optimal independent variable layer set corresponding to the first-level region; and then, proceeding to Step K;

Step K, if R_OLS≥R_NLS, for the sampling sites corresponding to the first-level region, deriving data values of independent variables from the optimal independent variable layer set, and training a linear regression model between the data values of the independent variables in the optimal independent variable set and the data values of the soil dependent variables, to form a first-level region prediction model; and then, proceeding to Step L;

if R_NLS>R_OLS, for the sampling sites corresponding to the first-level region, deriving data values of independent variables from the optimal independent variable layer set, and training a nonlinear regression model between the data values of the independent variables in the optimal independent variable set and the data values of the soil dependent variables, to form a first-level region prediction model; and then, proceeding to Step L;

Step L, generating, according to the optimal independent variable layer set corresponding to the first-level region, a spatial distribution map of the soil dependent variable, namely, a spatial distribution map of the target soil property in the target region, by applying independent variables from the optimal independent variable layer set into the first-level region prediction model, to realize prediction of the target soil property in the target region;

Step M, for each second-level region, acquiring an optimal independent variable layer set corresponding to the each second-level region by using the method descried in Steps I to J; and then, proceeding to Step N;

Step N, if R_OLS_mean≥R_NLS_mean, for each second-level region and for the sampling sites corresponding to the second-level region, deriving data values of independent variables from the optimal independent variable set corresponding to the second-level region, and training a linear regression model between the data values of the independent variables and the data values of the soil dependent variables, to form a second-level region prediction model, thus obtaining the second-level region prediction model for each of the second-level region; and then, proceeding to Step O;

if R_NLS_mean>R_OLS_mean, for each second-level region and for the sampling sites corresponding to the second-level region, deriving data values of independent variables from the optimal independent variable set corresponding to the second-level region, and training a nonlinear regression model between the data values of the independent variables and the data values of the soil dependent variables, to form a second-level region prediction model, thus obtaining second-level region prediction model for each of the second-level regions; and then, proceeding to Step O; and Step O, generating, for each second-level region, according to the optimal independent variable layer set corresponding to the second-level region, a spatial distribution map of the soil dependent variable in the second-level region by applying the second-level region prediction model, thus obtaining a spatial distribution map of the soil dependent variable in each of the second-level regions; and obtaining a spatial distribution map of the target soil property in the target region after combination, to predict the target soil property in the target region.

As a preferred technical solution of the present disclosure, the method further includes Steps H-I and H-M, and Step H is as follows:

Step H, if there is no second-level region, proceeding to Step H-I;

if there are second-level regions, when R_OLS is greater than both R_OLS_mean and R_NLS_mean or R_NLS is greater than both R_OLS_mean and R_NLS_mean, proceeding to Step H-I; and when R_OLS_mean is greater than both R_OLS and R_NLS or R_NLS_mean is greater than both R_OLS and R_NLS, proceeding to Step H-M;

Step H-I, if R_OLS≥R_NLS, for the sampling sites which lack the data values of the soil dependent variables in the target region, predicting and adding the data values of the soil dependent variables by applying the linear regression model corresponding to the first-level region in Step G; and then proceeding to Step I;

if R_NLS>R_OLS, for the sampling sites which lack the data values of the soil dependent variables in the target region, predicting and adding the data values of the soil dependent variables by applying the nonlinear regression model corresponding to the first-level region in Step G; and then proceeding to Step I;

Step H-M, if R_OLS_mean≥R_NLS_mean, for the sampling sites which lack the data values of the soil dependent variables in the target region, predicting and adding the data values of the soil dependent variable by applying the linear regression model corresponding to the second-level regions in Step G; and then proceeding to Step M; and if R_NLS_mean≥R_OLS_mean, for the sampling sites which lack the data values of the soil dependent variables in the target region, predicting and adding the data values of the soil dependent variables by applying the nonlinear regression model corresponding to the second-level regions in Step G; and then proceeding to Step M.

As a preferred technical solution of the present disclosure, Step A includes the following steps:

Step A1, collecting data values of the preset soil physicochemical properties comprising the target soil property for presetting sampling sites in the target region, according to existing soil data in specified data sources; and then, proceeding to Step A2;

Step A2, selecting the sampling sites of which the data values of the corresponding soil physicochemical properties are non-null, and partitioning a first-level region with a smallest bounding polygon covering all the selected sampling sites, wherein the sampling sites are used as the sampling sites corresponding to the first-level region; and then, proceeding to Step A3; and Step A3, defining the soil dependent variable as the target soil property, and rest of the soil physicochemical properties than the target soil property are used to form a soil independent variable set; and then, proceeding to Step B.

As a preferred technical solution of the present disclosure, Step B includes the following steps:

Step B1, acquiring layers, covering the first-level region, of the specified environmental variables related to the soil dependent variable, and then proceeding to Step B2;

Step B2, separately converting the layers of the specified environmental variables to environmental variable grid layers, wherein if the specified environmental variables comprise at least one waveband, each waveband in the specified environmental variables is converted to a corresponding environmental variable grid layer; and then, proceeding to Step B3;

Step B3, resampling for all the environmental variable grid layers by means of bilinear interpolation, and unifying a spatial resolution of grid data to a preset spatial resolution; and then, proceeding to Step B4;

Step B4, acquiring areas corresponding to the first-level region on the environmental variable grid layers, and for the sampling sites corresponding to the first-level region, deriving values from the specified environmental variables at the sampling sites; and then, proceeding to Step B5; and Step B5, adding the derived values to the soil independent variable set, to update the soil independent variable set; and then, proceeding to Step C.

As a preferred technical solution of the present disclosure, Step C includes the following steps:

Step C1, for the sampling sites corresponding to the first-level region, training a linear regression model between the soil dependent variables and the independent variables in the soil independent variable set, and acquiring a coefficient of determination of the independent variables in the soil independent variable set, wherein denotes a coefficient of determination of the kth independent variable in the soil independent variable set; and then, proceeding to Step C2;

Step C2, for the independent variables in the soil independent variable set, acquiring a coefficient of variance expansion of the independent variables according to a calculation result of; and then, proceeding to Step C3;

Step C3, determining whether the coefficients of variance expansion of the independent variables in the soil independent variable set are all less than a preset coefficient threshold, and proceeding to Step C4 if yes; or otherwise, deleting an independent variable with the largest coefficient of variance expansion from the soil independent variable set to update the soil independent variable set, and returning to Step C1; and Step C4, for the sampling sites corresponding to the first-level region, calculating the correlations between the data values of the soil dependent variables and the data values of the independent variables in the soil independent variable set, and deleting the independent variables of which the correlation is less than the preset significant difference threshold of in correlation from the soil independent variable set, to update the soil independent variable set; and then, proceeding to Step D.

As a preferred technical solution of the present disclosure, in Step D, after completion of training for the preset number of iterations, the temporary optimal independent variable set which is most frequently screened is adopted as a candidate optimal independent variable set corresponding to the first-level region; and Step D further includes the following steps:

Step D1, for the sampling sites corresponding to the first-level region, continuously training a linear relationship between the soil dependent variables and the soil independent variables in the soil independent variable set by using the stepwise multiple linear regression model and based on a preset number of incremental iterations; separately acquiring a temporary optimal independent variable set during each iterative training, and continuously recording the selection number of each of the temporary optimal independent variable sets; after completion of training for the preset number of iterations, adopting the temporary optimal independent variable set which is mostly frequently screened as a candidate optimal independent variable set corresponding to the first-level region; and then, proceeding to Step D2; and Step D2, determining whether the two latest obtained candidate optimal independent variable sets corresponding to the first-level region are consistent, and if yes, adopting the candidate optimal independent variable set as the optimal independent variable set corresponding to the first-level region, and proceeding to Step E; or otherwise, returning to Step D1.

As a preferred technical solution of the present disclosure, Step E includes the following steps:

Step E1, acquiring a land use layer and a soil-forming parent material layer that cover the first-level region, and for the sampling sites corresponding to the first-level region, extracting a land use zone and a soil-forming parent material zone where the sampling sites are located; and then, proceeding to Step E2;

Step E2, analyzing and obtaining, based on the data values of the soil dependent variable at the sampling sites corresponding to the first-level region, difference results in the soil dependent variable between the different land use zones and difference results in the soil dependent variable between the different soil-forming parent material zones by means of Duncan multiple comparison analysis; and then, proceeding to Step E3;

Step E3, if none of the difference results in the soil dependent variable between the different land use zones and the difference results in the soil dependent variable between the different soil-forming parent material zones are greater than a preset significant difference threshold, proceeding to Step G; or otherwise, proceeding to Step E4;

Step E4, if there is a difference result greater than the preset significant difference threshold in the difference results in the soil dependent variable between the different land use zones, and none of the difference results in the soil dependent variable between the different soil-forming parent material zones are greater than the preset significant difference threshold, merging the different land use zones with the difference results not greater than the preset significant difference threshold to partition the second-level regions; and then, proceeding to Step E7; or otherwise, proceeding to Step E5;

Step E5, if there is a difference result greater than the preset significant difference threshold in the difference results in the soil dependent variable between the different soil-forming parent material zones, and none of the difference results in the soil dependent variable between the different land use zones are greater than the preset significant difference threshold, merging the different soil-forming parent material zones with the difference results not greater than the preset significant difference threshold to partition the second-level regions; and then, proceeding to Step E7; or otherwise, proceeding to Step E6;

Step E6, if there is a difference result greater than the preset significant difference threshold in both the difference results in the soil dependent variable between the different soil-forming parent material zones and the difference results in the soil dependent variable between the different land use zones, merging the different soil-forming parent material zones with the difference results not greater than the preset significant difference threshold to partition the second-level regions, and merging the different land use zones with the difference results not greater than the preset significant difference threshold to partition the second-level regions; and then, proceeding to Step E7; and Step E7, partitioning the second-level regions by performing spatial overlay for the second-level regions partitioned after merging in the land use layer and the land use zones that are not merged and for the second-level regions partitioned after merging in the soil-forming parent material layer and the soil-forming parent material zones that are not merged; and acquiring the sampling sites corresponding to each of the second-level regions based on the sampling sites corresponding to the first-level region; and then, proceeding to Step F.

As a preferred technical solution of the present disclosure, Step G includes the following steps:

Step G1, among the sampling sites corresponding to the first-level region, grouping the sampling sites with a first preset proportion as a training sample and grouping the sampling sites remained as a verification sample, wherein the first preset proportion is greater than 50%; and then, proceeding to Step G2;

Step G2, for the sampling sites in the training sample, training a linear regression model OLS between the data values of the soil dependent variables and the data values of independent variables in the corresponding optimal independent variable set, and then, proceeding to Step G3;

Step G3, for data values of independent variables in the optimal independent variable set corresponding to the sampling sites in the verification sample, obtaining predicted data values of the soil dependent variables at the sampling sites in the verification sample by applying the linear regression model OLS; and then proceeding to Step G4;

Step G4, calculating, for the sampling sites in the verification sample, a coefficient of determination between the data values of the soil dependent variables and the corresponding predicted data values of the soil dependent variables, which is termed R_OLS of the linear regression model corresponding to the first-level region; and then proceeding to Step G5;

Step G5, for the independent variables in the optimal independent variable set corresponding to the first-level region, performing fitting of preset specified functions for the data values of the soil dependent variables at the sampling sites in the training sample and the data values of the corresponding independent variables; selecting a function with the highest prediction accuracy as a nonlinear fitting manner corresponding to the independent variable, thus obtaining nonlinear fitting manners respectively corresponding to the independent variables in the optimal independent variable set; and then, proceeding to Step G6;

Step G6, according to the nonlinear fitting manners respectively corresponding to the independent variables in the optimal independent variable set corresponding to the first-level region, for the sampling sites in the training sample, training a nonlinear regression model NLS between the data values of the soil dependent variables and the data values of the independent variables in the corresponding optimal independent variable set by using the nonlinear least square method; and then, proceeding to Step G7;

Step G7, for the data values of independent variables in the optimal independent variable set corresponding to the sampling sites in the verification sample, obtaining predicted data values of the soil dependent variables at the sampling sites in the verification sample by applying the nonlinear regression model NLS; and then proceeding to Step G8;

Step G8, calculating, for the sampling sites in the verification sample, a coefficient of determination between the data values of the soil dependent variables and the predicted data value of the soil dependent variable, which is termed R_NLS of the nonlinear regression model corresponding to the first-level region; and then proceeding to Step G9;

Step G9, if there is no second-level region, proceeding to Step H directly; or if there are second-level regions, proceeding to Step G10; and Step G10, Performing, for all the second-level regions, Steps G1 to G8, to acquire the coefficients of determination of linear regression models and nonlinear regression models corresponding to all the second-level regions and to further acquire the mean values of these coefficients of determination of linear regression models and nonlinear regression models corresponding to all the second-level regions, which are termed R_OLS_mean and R_NLS_mean, respectively, and then, proceeding to Step H.

As a preferred technical solution of the present disclosure, Step I includes the following steps:

Step I1, based on the sampling sites corresponding to the first-level region and the corresponding optimal independent variable set, for the soil physicochemical properties in the optimal independent variable set, separately training specified prediction models by means of 10-fold cross-validation according to the data values of the soil physicochemical properties corresponding to the sampling sites and the data values of the specified environmental variables in Step B, to obtain different prediction models; selecting a prediction model with the highest prediction accuracy as a prediction model based on all the specified environmental variables in Step B for the soil physicochemical property, thus obtaining prediction models based on all the specified environmental variables in Step B for the different soil physicochemical properties in the optimal independent variable set; and then, proceeding to Step I2; and Step I2, according to the prediction model based on all the specified environmental variables in Step B for the soil physicochemical properties in the optimal independent variable set corresponding to the first-level region with each the layers of specified environment variables in Step B, generating spatial distribution prediction layer of the soil physicochemical properties in the optimal independent variable set corresponding to the first-level region according to the layers of the specified environmental variables in Step B.

Compared to the prior art, the PTF-based method for predicting a target soil property and content described in the present disclosure has the following technical effects:

(1) In the PTF-based method for predicting a target soil property and content designed in the present disclosure, the proposed PTFs at the sampling site scale can fully utilize the existing geographic element information, and solve the problem of low accuracy in prediction of the target soil property and content, thus being directly applicable for monitoring, supplement, and update of the national natural resource survey data, and further providing technical service for data supplementation in dynamic simulation of ecological models and surface process. Especially, the dynamic screening mechanism for environmental variables in the prediction process corrects the limitations of the conventional prediction technology and realizes a universal soil property prediction technology with "limited resources and multi-source applications", thus having a broad industrial application prospect in agricultural application and land resource departments.

(2) In the PTF-based method for predicting a target soil property and content designed in the present disclosure, the proposed zoning mechanism based on spatial variation in the target soil property and content can accurately measure the uncertainty of the variables and the prediction functions during fitting of the PTFs and technical regulations for dynamical screening of the optimal independent variable set. Thus, the uncertainty in the relevant production process can be quantified, and further the optimal dependent variable set required for the PTFs can be determined to the greatest extent, thus significantly improving the universality and stability of the present disclosure.

(3) The PTF-based method for predicting a target soil property and content designed in the present disclosure differs from the conventional method using the PTFs oriented toward the sampling sites, and proposes a technical process which covers a mapping mechanism between soil maps and the measured soil physicochemical properties. Therefore, the method of the present disclosure can improve the PTFs at the sampling site scale, and optimize the compatibility of the function parameters with the soil maps, thus raising the scale of the fitted functions to different study areas and realizing production of regional-scale soil maps. This technology makes full use of the technical advantages of the existing geographic information system and can provide more urgent soil map products for more application departments.

DESCRIPTION OF THE EMBODIMENTS

The specific implementation of the present disclosure is further described in detail below with reference to the accompanying drawings of the specification.

The present disclosure designs a PTF-based method for predicting a target soil property and content, which has the following basic idea: based on collection of a multi-source soil dataset and environmental variables, dividing a dataset containing all measured information; partitioning second-level regions by zoning according to the spatial variation in the soil properties, obtaining an optimal independent variable set of PTFs in different regions by screening, and then performing linear and nonlinear fitting of the PTFs for different zones separately; by comparing the accuracy of different functions between different zones, selecting optimal PTFs oriented toward sampling sites, so as to build a database including soil sampling sites; and constructing a regional soil map by means of relatively mature machine learning, deriving laboratory analysis data of the soil sampling sites and data about the soil map, analyzing errors in the data by comparison, updating and training the PTFs oriented toward the sampling sites into region-oriented PTFs, and generating a spatial distribution map of the target soil property and content in a target region, wherein, the soil property includes physicochemical properties, for example, concentration, content, or the like, more specifically such as organic carbon concentration, phosphorus storage, pH, or the like.

Figure 1:
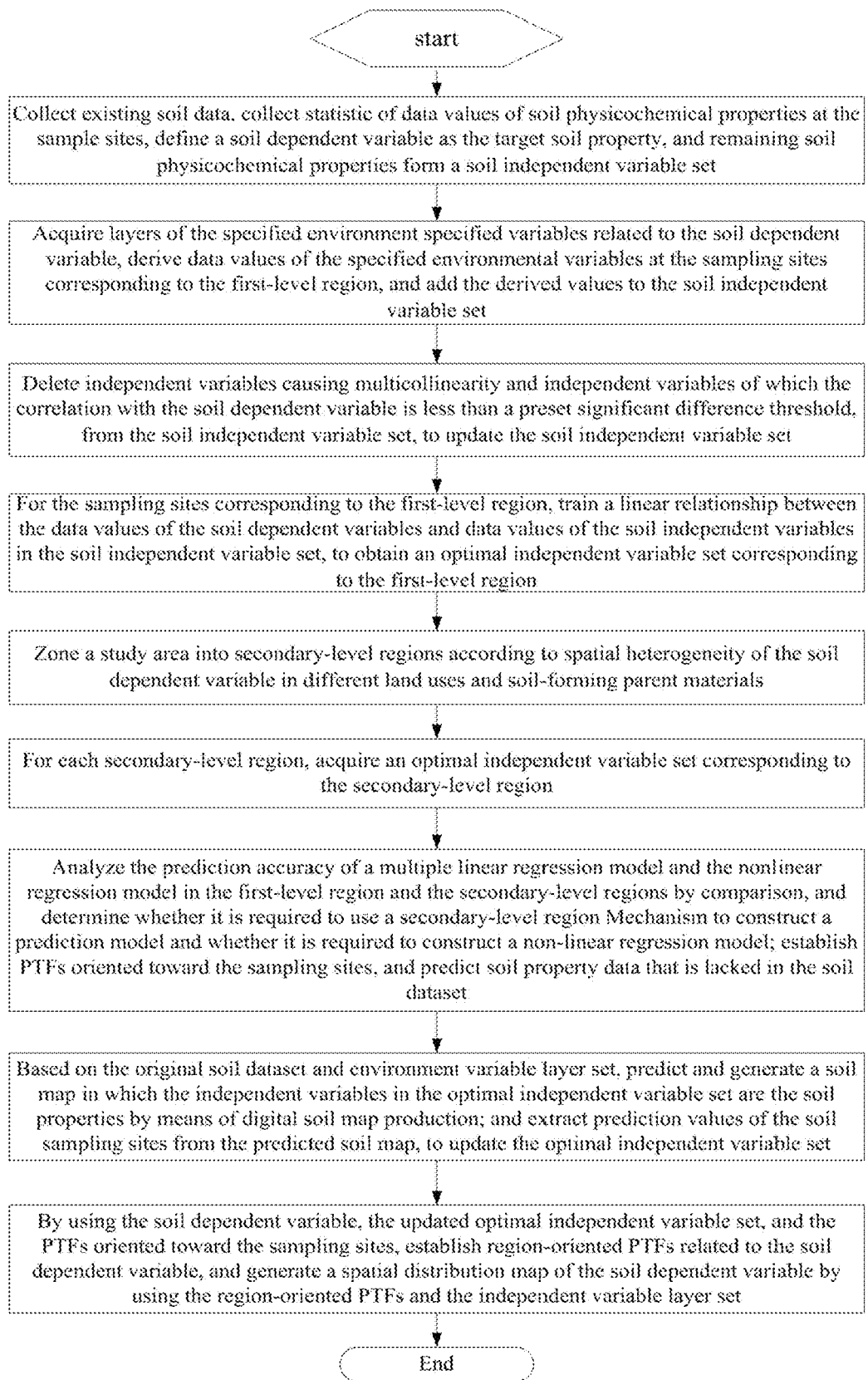
FIG. 1 shows a flowchart of steps of a PTF-based method for predicting a target soil property and content designed by the present disclosure.

The present disclosure designs a PTF-based method for predicting a target soil property and content, which is used to realize prediction of the target soil property and content in a target region. In actual application, as shown in FIG. 1, following Steps A to O are specifically performed:

Step A. Selecting, based on existing soil data, selecting sampling sites of which the data values of corresponding preset soil physicochemical properties are non-null from the target region, and partitioning a first-level region with a smallest bounding polygon covering all the selected sampling sites, wherein the sampling sites are used as sampling sites corresponding to the first-level region, and the preset soil physicochemical properties comprise a target soil property that is referred to as a soil dependent variable and is defined as the target soil property, and rest of the soil physicochemical properties that are used to form a soil independent variable set. Then, the process proceeds to Step B.

In specific implementation, foregoing Step A specifically includes following Steps A1 to A3.

Figures 2, 3:
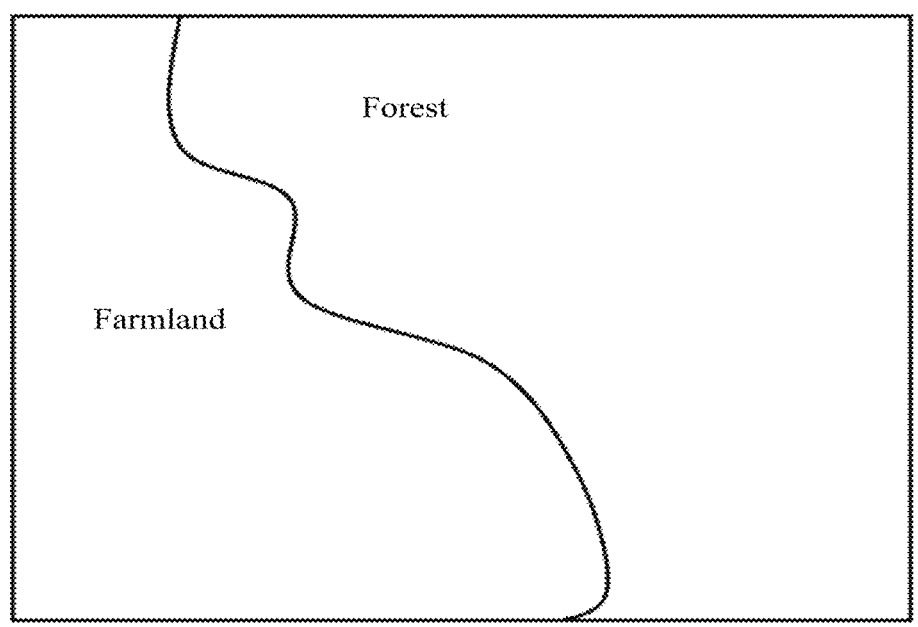
FIG. 2 is a schematic diagram of construction of an original soil dataset and a core soil dataset in the present disclosure.
FIG. 3 is a schematic diagram of zoning for second-level regions covering two land use types in the present disclosure.

Step A1. Data values of the preset soil physicochemical properties comprising the target soil property for presetting sampling sites in the target region are collected, according to existing soil data in specified data sources, as shown in FIG. 2, where S_1, S_2, S_3, S_4, and S_5 are the soil physicochemical properties. Then, the process proceeds to Step A2.

For the data values of the preset soil physicochemical properties, data values at the same soil depth are selected, for example, data values of the soil physicochemical properties at a depth of 0-1 m or 0-20 cm in a soil profile are selected.

Step A2. Sampling sites of which the data values of the corresponding soil physicochemical properties are non-null are selected, and a smallest bounding polygon covering all the selected sampling sites are partitioned a first-level region, where the sampling sites are used as sampling sites corresponding to the first-level region. Then, the process proceeds to Step A3.

Step A3. The soil dependent variable is defined as the target soil property, and rest of the soil physicochemical properties excluding the target soil property are used to form a soil independent variable set. Then, the process proceeds to Step B.

Step B. Layers, covering the first-level region, of specified environmental variables related to the soil dependent variable are acquired. For the sampling site corresponding to the first-level region, values from the specified environmental variables at the sampling site are derived, and the derived values are added to the soil independent variable set, to update the soil independent variable set. Then, the process proceeds to Step C.

In specific implementation, foregoing Step B specifically includes following Steps B1 to B5.

Step B1. Layers, covering the first-level region, of the specified environmental variables related to the soil dependent variable are acquired, and then the process proceeds to Step B2. These environmental variables affect the formation and evolution of the soil to a certain extent. Refer to the following table 1 for some optional environmental variable layers.

TABLE 1

| D | Variable names | Types | Information described in the layers |
|---|---|---|---|
| | Soil temperature | Climate | Temperature of soil at 50 cm |
| | Mean annual precipitation | Climate | Long-time mean annual value, which indicates the amount of precipitation per year in an area and is the depth of precipitation that accumulates on a horizontal plane |
| | Mean annual temperature | Climate | Mean temperature of an area in a year during a certain period of time |
| | Accumulated temperature ≥ | Climate | Sum of the daily mean temperatures in duration during which |

TABLE 1-continued

| D | Variable names | Types | Information described in the layers |
|---|---|---|---|
| | 0° C. | | the mean temperature of each day is ≥0° C. in a period of time |
| | Accumulated temperature ≥ 10° C. | Climate | Sum of the daily mean temperatures in duration during which the mean temperature of each day is ≥0° C. in a period of time |
| | Mean annual sunshine | Climate | Mean of sunshine times in a year |
| | Annual evaporation | Climate | Amount of water dispersed into the atmosphere after evaporation during a certain period of time |
| | Number of frost-free days | Climate | Long-time mean annual value, which indicates the number of days without frost in a year |
| | Mean annual wind speed | Climate | Mean of instantaneous wind speeds in a year |
| 0 | Humidity index | Climate | Expression manner to measure the degree of humidity, which can be calculated by using the ratio of the intake to the loss of ground moisture |
| 1 | Normalized difference vegetation index | Remote sensing factor | Variable layer calculated based on a remote sensing layer, which can show vegetation coverage conditions on the surface |
| 2 | Difference environmental vegetation index | Remote sensing factor | which reflects the sensitivity to soil background changes by calculation of reflectance of two wavebands |
| 3 | Ratio vegetation index | Remote sensing factor | which is the ratio of the reflectance of the two wavebands and characterizes the green plant |
| 4 | Net primary productivity | Remote sensing factor | Ability of green plants to produce organic carbon through photosynthesis |
| 5 | Elevation | Topography | Altitude |
| 6 | Aspect | Topography | Direction of the projection of the normal to the slope on the horizontal plane |
| 7 | Slope | Topography | Quantitative expression of the steepness of surface units |
| 8 | Topographic wetness index | Topography | Dry and wet conditions of soil moisture in the watershed |
| 9 | Slope length | Topography | Length of the projection of the maximum ground distance from a point on the ground to the starting point of the flow direction along the direction of water flow on the horizontal plane |
| 0 | Mean annual fertilizer application | Artificial disturbance | Regional mean annual fertilizer application in different crop areas |

Note:
The environmental variable layer may be in a Shapefile data format of vectors or a grid format (for example, TIFF or Grid).

Step B2. The layers of the specified environmental variables are separately converted to environmental variable grid layers, where if the environmental variables include at least one waveband, each waveband in the environmental variables is converted to a corresponding environmental variable grid layer. Then, the process proceeds to Step B3.

Step B3. All the environmental variable grid layers are resampled by means of bilinear interpolation, and a spatial resolution of grid data is unified to a preset spatial resolution. Then, the process proceeds to Step B4. For example, if a grid has a coverage area of 100 m×100 m, its spatial resolution is 100 m. A higher grid resolution indicates a higher spatial detailed degree of elements.

In actual application, the resampling method for the grid data is not limited to the bilinear interpolation; and the nearest neighbor method, cubic convolution interpolation method, and other technologies may also be used.

Figure 6:
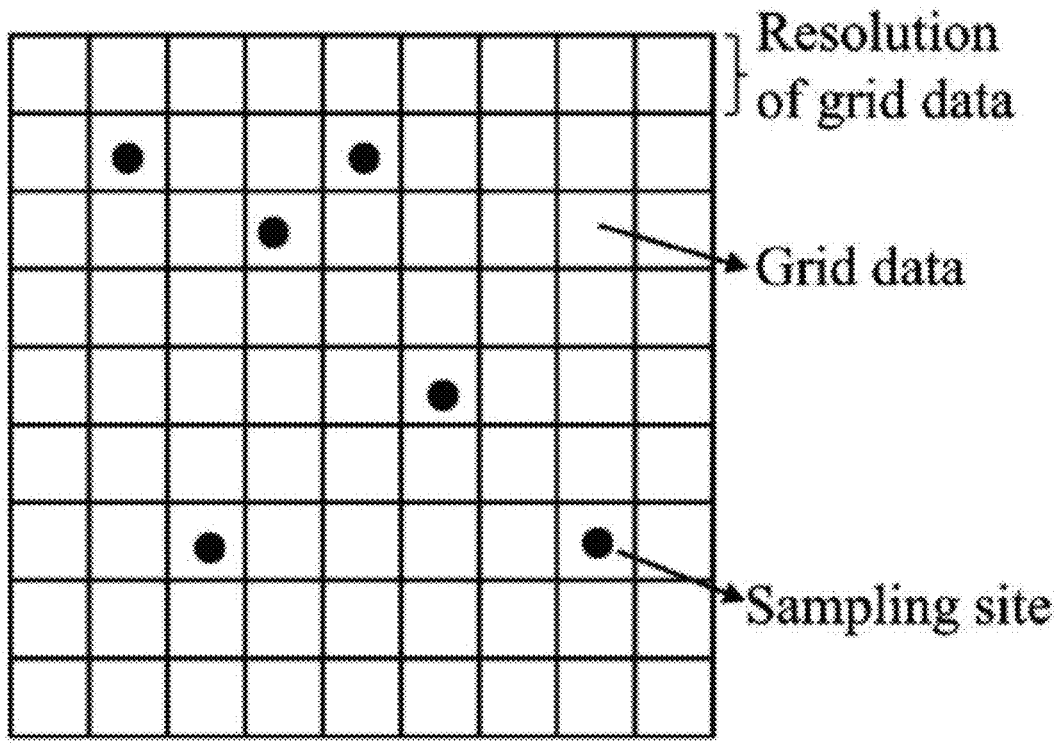
FIG. 6 is a schematic diagram of a grid environmental variable layer and soil sampling sites in the present disclosure.

In actual application, a schematic diagram of the obtained grid environmental variable layer and the soil sampling sites is shown by FIG. 6.

Step B4. Areas corresponding to the first-level region on the environmental variable grid layers are acquired, and for the sampling sites corresponding to the first-level region, data values from the specified environmental variables at the sampling site are derived. Then, the process proceeds to Step B5.

Step B5. The data values derived in Step 4 are added to the soil independent variable set, to update the soil independent variable set. Then, the process proceeds to Step C.

Step C. Independent variables causing multicollinearity and independent variable of which the correlation with the soil dependent variable is less than a preset significant difference threshold, from the soil independent variable set to update the soil independent variable set. Then, the process proceeds to Step D.

In specific implementation, the foregoing Step C specifically includes following Steps C1 to C4.

Step C1. For the sampling sites corresponding to the first-level region, a linear regression model between the soil dependent variable and the independent variables in the soil independent variable set is trained, and a coefficient $R_k^2$ of determination of the independent variable in the soil independent variable set is acquired, where $R_k^2$ denotes a coefficient of determination of the kth independent variable in the soil independent variable set. Then, the process proceeds to Step C2.

Step C2. For these independent variables in the soil independent variable set, a coefficient of variance expansion of the independent variable is acquired according to a calculation result of $$\frac{1}{1-R_k^2}.$$

Then, the process proceeds to Step C3.

Step C3. It is determined whether the coefficients of variance expansion of the independent variables in the soil independent variable set are all less than a preset coefficient threshold, where the preset coefficient threshold is, for example, 5; the process proceeds to Step C4 if yes; or otherwise, an independent variable with the largest coefficient of variance expansion is deleted from the soil independent variable set to update the soil independent variable set, and the process returns to Step C1.

Step C4. For the sampling sites corresponding to the first-level region, the correlations between the data values of the soil dependent variables and the data values of the independent variables in the soil independent variable set are calculated, and the independent variables of which the correlation is less than the preset significant difference threshold are deleted from the soil independent variable set, to update the soil independent variable set. Then, the process proceeds to Step D.

Step D. For the sampling sites corresponding to the first-level region, a linear relationship between the soil dependent variables and the soil independent variables in the soil independent variable set is trained by using a stepwise multiple linear regression model and based on a preset number of iterations, for example, 100 iterations. A temporary optimal independent variable set obtained by screening during each iterative training operation is separately acquired, and a selection number of each of the temporary optimal independent variable sets is recorded. After completion of training for the preset number of iterations, the most frequently screened temporary optimal independent variable set is adopted as an optimal independent variable set corresponding to the first-level region. Then, following Steps D1 and D2 are further performed.

Step D1. For the sampling sites corresponding to the first-level region, a linear relationship between the soil dependent variables and the soil independent variables in the soil independent variable set is trained continuously by using the stepwise multiple linear regression model and based on a preset number of incremental iterations, for example, 50 iterations. A temporary optimal independent variable set obtained by screening during each iterative training operation is separately acquired, and a selection number of each of the temporary optimal independent variable sets is separately recorded. After completion of training for the preset number of incremental iterations, the most frequently selected temporary optimal independent variable set is used as a candidate optimal independent variable set corresponding to the first-level region. Then, the process proceeds to Step D2.

Step D2. It is determined whether the two latest obtained candidate optimal independent variable sets corresponding to the first-level region are consistent, and if yes, the candidate optimal independent variable set is adopted as the optimal independent variable set corresponding to the first-level region, and the process proceeds to Step E; or otherwise, the process returns to Step D1.

Step E. Layers of a soil region with preset properties that cover the first-level region are acquired, and for the sampling sites corresponding to the first-level region, soil zones with the preset properties where the sampling site is located are extracted. Based on the data value of the soil dependent variable at the sampling site, difference results in the soil dependent variable between different soil zones are analyzed and obtained, and if none of the difference results are greater than the preset significant difference threshold, the process proceeds to Step G. If there is a difference result greater than the preset significant difference threshold in the obtained difference results, the soil zones with the difference results not greater than the preset significant difference threshold are merged, and in combination with the soil zones that are not merged, second-level regions are partitioned; and based on the sampling sites corresponding to the first-level region, sampling sites corresponding to the second-level regions are acquired. Then, the process proceeds to Step F.

In specific implementation, the foregoing Step E specifically includes following Steps E1 to E7.

Step E1. A land use layer and a soil-forming parent material layer that cover the first-level region are acquired, and for the sampling sites corresponding to the first-level region, a land use zone and a soil-forming parent material zone where the sampling sites are located are extracted. Then, the process proceeds to Step E2.

Step E2. Based on the data values of the soil dependent variable at the sampling sites corresponding to the first-level region, difference results in the soil dependent variable between the different land use zones and difference results in the soil dependent variable between the different soil-forming parent material zones are analyzed and obtained by means of Duncan multiple comparison analysis. Then, the process proceeds to Step E3.

Step E3. If none of the difference results in the soil dependent variable between the different land use zones and the difference results in the soil dependent variable between the different soil-forming parent material zones are greater than a preset significant difference threshold, the process proceeds to Step G; or otherwise, the process proceeds to Step E4.

Step E4. If there is a difference result greater than the preset significant difference threshold in the difference results in the soil dependent variable between the different land use zones, and none of the difference results in the soil dependent variable between the different soil-forming parent material zones are greater than the preset significant difference threshold, the different land use zones with the difference results not greater than the preset significant difference threshold are merged to partition the second-level regions. Then, the process proceeds to Step E7; or otherwise, the process proceeds to Step E5.

Step E5. If there is a difference result greater than the preset significant difference threshold in the difference results in the soil dependent variable between the different soil-forming parent material zones, and none of the difference results in the soil dependent variable between the different land use zones are greater than the preset significant difference threshold, the different soil-forming parent material zones with the difference results not greater than the preset significant difference threshold are merged to partition the second-level regions. Then, the process proceeds to Step E7; or otherwise, the process proceeds to Step E6.

Step E6. If there is a difference result greater than the preset significant difference threshold in both the difference results in the soil dependent variable between the different soil-forming parent material zones and the difference results in the soil dependent variable between the different land use zones, the different soil-forming parent material zones with the difference results not greater than the preset significant difference threshold are merged to partition the second-level regions, and the different land use zones with the difference results not greater than the preset significant difference threshold are merged to partition the second-level regions. Then, the process proceeds to Step E7.

Step E7. Spatial overlay is performed for the second-level regions partitioned after merging in the land use layer and the land use zones that are not merged and for the second-level regions partitioned after merging in the soil-forming parent material layer and the soil-forming parent material zones that are not merged, to partition the second-level regions; and the sampling sites corresponding to each of the second-level regions are acquired based on the sampling sites corresponding to the first-level region. Then, the process proceeds to Step F.

Figure 4:
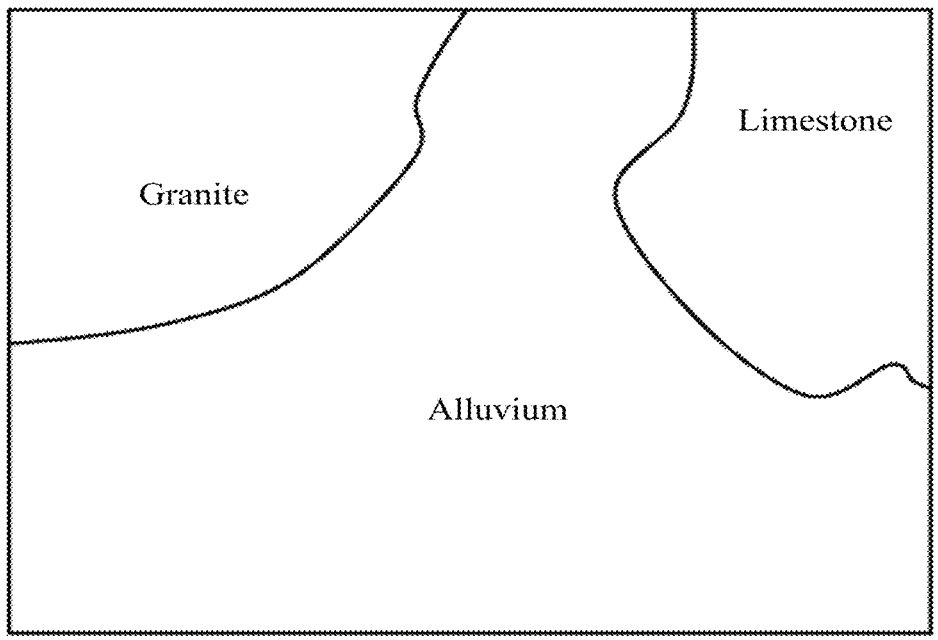
FIG. 4 is a schematic diagram of zoning for second-level regions covering three types of soil-forming parent materials in the present disclosure.
Figure 5:
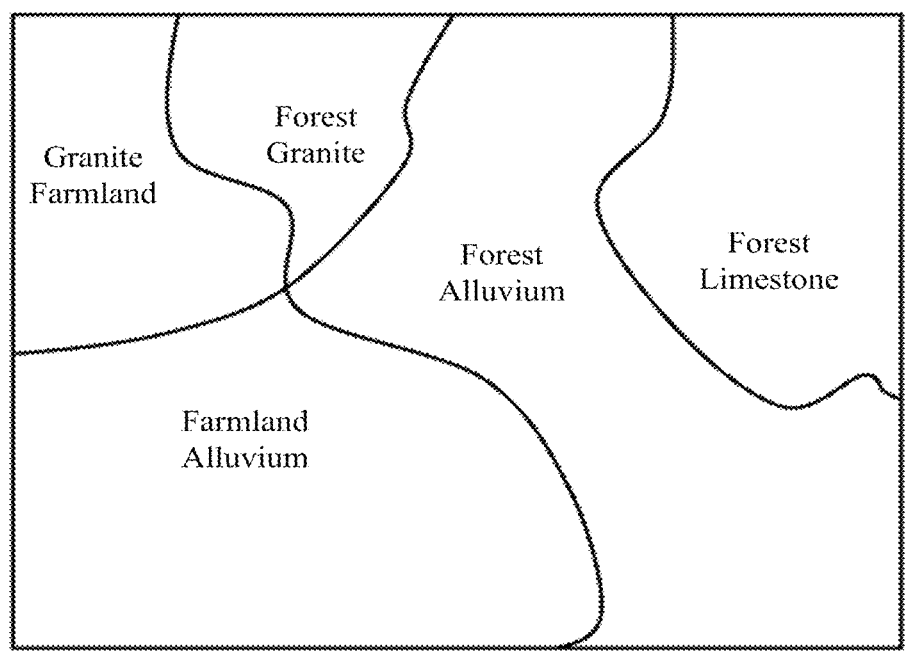
FIG. 5 is a schematic diagram of zoning for second-level regions covering two land use types and three types of soil-forming parent materials in the present disclosure.

In actual application, zoning for the second-level regions covering two land use types is shown by FIG. 3, zoning for the second-level regions covering three types of soil-forming parent materials is shown by FIG. 4, and zoning for the second-level regions covering two land use types and three types of soil-forming parent materials is shown by FIG. 5.

Step F. For each of the second-level regions, an optimal independent variable set corresponding to each of the second-level region is acquired by using the method described in Step D, and then the process proceeds to Step G.

Step G. For the sampling site corresponding to the first-level region, a linear regression model and a nonlinear regression model between the data value of the soil dependent variable and the data values of independent variables in the corresponding optimal independent variable set are trained; and the coefficient of determination of the linear regression model and that of the nonlinear regression model are acquired, where, the coefficient of determination of the linear regression model corresponding to the first-level region is R_OLS and the coefficient of determination of the nonlinear regression model is R_NLS.

Further, if there is no second-level region, the process directly proceeds to Step H. If there are second-level regions, for the second-level region, a linear regression model and a nonlinear regression model between the data value of the soil dependent variable at each sampling site and the data values of the independent variables in the corresponding optimal independent variable set are trained separately, and the coefficient of determination of the linear regression model and that of the nonlinear regression model are acquired. Thus, coefficients of determination of the linear regression models and the nonlinear regression models corresponding to all the second-level regions are acquired, and mean values of these coefficients of determination of the linear regression models and nonlinear regression models corresponding to all the second-level regions, which are termed R_OLS_mean and R_NLS_mean, respectively. Then, the process proceeds to Step H.

In specific implementation, foregoing Step G specifically includes following Steps G1 to G10.

Step G1. Among the sampling sites corresponding to the first-level region, the sampling sites with a first preset proportion are grouped as a training sample and the sampling sites remained are grouped as a verification sample, where the first preset proportion is greater than 50%, for example, 75%. Then, the process proceeds to Step G2.

Step G2. For the sampling sites in the training sample, a linear regression model OLS between the data value of the soil dependent variable and the data values of independent variables in the corresponding optimal independent variable set is trained, and then the process proceeds to Step G3.

Step G3. For data values of independent variables in the optimal independent variable set corresponding to each sampling site in the verification sample, a predicted data value of the soil dependent variable at the sampling site in the verification sample is obtained by applying the linear regression model OLS; and then the process proceeds to Step G4.

Step G4. For the sampling sites in the verification sample, a coefficient of determination between the data values of the soil dependent variables and the corresponding predicted data value of the soil dependent variable, which is termed R_OLS of the linear regression model corresponding to the first-level region, is calculated; and then the process proceeds to Step G5.

Step G5. For the independent variables in the optimal independent variable set corresponding to the first-level region, fitting of preset specified functions are performed for the data values of the soil dependent variables at the sampling sites in the training sample and the data values of the corresponding independent variables, where the preset specified functions include, for example, a power function, an exponential function, a hyperbolic function, and a logarithmic function. Then, a function with the highest prediction accuracy is selected as a nonlinear fitting manner corresponding to this independent variable, thus obtaining nonlinear fitting manners respectively corresponding to the independent variables in the optimal independent variable set. Then, the process proceeds to Step G6.

Step G6. According to the nonlinear fitting manners respectively corresponding to the independent variables in the optimal independent variable set corresponding to the first-level region, for the sampling sited in the training sample, a nonlinear regression model NLS between the data values of the soil dependent variables and the data values of the independent variables in the corresponding optimal independent variable set is trained by using the nonlinear least square method. Then, the process proceeds to Step G7.

Step G7. For the data values of independent variables in the optimal independent variable set corresponding to the sampling sites in the verification sample, predicted data values of the soil dependent variables at the sampling sites in the verification sample are obtained by applying the nonlinear regression model NLS; and then the process proceeds to Step G8.

Step G8. For the sampling sites in the verification sample, a coefficient of determination between the data values of the soil dependent variables and the corresponding predicted data values of the soil dependent variables, which is termed R_NLS of the nonlinear regression model corresponding to the first-level region, is calculated; and then the process proceeds to Step G9.

Step G9. If there is no second-level region, the process directly proceeds to Step H; or if there are second-level regions, the process proceeds to Step G10.

Step G10. For all the second-level region, the method described in Steps G1 to G8 is performed, to acquire the coefficients of determination of linear regression models and nonlinear regression models corresponding to all the second-level regions, and to further obtain the mean values of these coefficients of determination of linear regression models and nonlinear regression models corresponding to all the second-level regions, which are termed R_OLS_mean and R_NLS_mean, respectively. Then, the process proceeds to Step H.

Step H. If there is no second-level region, the process proceeds to Step H-I; if there are second-level regions, when R_OLS is greater than both R_OLS_mean and R_NLS_mean or R_NLS is greater than both R_OLS_mean and R_NLS_mean, the process proceeds to Step H-I; and when R_OLS_mean is greater than both R_OLS and R_NLS or R_NLS_mean is greater than both R_OLS and R_NLS, the process proceeds to Step H-M.

Step H-I. If R_OLS≥R_NLS, for the sampling sites which lack the data values of the soil dependent variable in the target region, the data values of the soil dependent variable are predicted and added by applying the linear regression model corresponding to the first-level region in Step G; and then the process proceeds to Step I.

If R_NLS>R_OLS, for the sampling sites which lack the data values of the soil dependent variables in the target region, the data values of the soil dependent variables are predicted and added by applying the nonlinear regression model corresponding to the first-level region in Step G; and then the process proceeds to Step I.

Step H-M. If R_OLS_mean≥R_NLS_mean, for the sampling sites which lack the data value of the soil dependent variable in the target region, the data values of the soil dependent variables are predicted and added by applying the linear regression model corresponding to each second-level region in Step G; and then the process proceeds to Step M.

If R_NLS_mean>R_OLS_mean, for the sampling site which lack the data values of the soil dependent variables in the target region, the data values of the soil dependent variables are predicted and added by applying the nonlinear regression model corresponding to each second-level region in Step G; and then the process proceeds to Step M.

Step I. Based on the sampling sites corresponding to the first-level region and the corresponding optimal independent variable set, and according to data values of soil physicochemical properties in the optimal independent variable set corresponding to the sampling sites, a prediction model based on all the specified environmental variables in Step B for each soil physicochemical property in the optimal independent variable set is trained; and then spatial distribution prediction layers of the soil physicochemical properties in the optimal independent variable set corresponding to the first-level region are generated according to the layers of the specified environmental variables in Step B. Then, the process proceeds to Step J.

In specific implementation, foregoing Step I specifically includes following Steps I1 and I2.

Step I1. Based on the sampling sites corresponding to the first-level region and the corresponding optimal independent variable set, for the soil physicochemical properties in the optimal independent variable set, specified prediction models are separately trained by means of 10-fold cross-validation according to the data values of the soil physicochemical properties corresponding to the sampling sites and the data values of the specified environmental variables in Step B, to obtain different prediction models. Herein, the training for the prediction models is performed by means of, for example, geographically weighted regression, ordinary kriging, regression kriging, an artificial neural network, or an enhanced regression tree.

Afterwards, a prediction model with the highest prediction accuracy is selected as a prediction model based on all the specified environmental variables in Step B for the soil physicochemical property, thus obtaining prediction models based on all the specified environmental variables in Step B for the soil physicochemical properties in the optimal independent variable set. Then, the process proceeds to Step I2.

Step I2. According to the prediction model based on all the specified environmental variables in Step B for the soil physicochemical properties in the optimal independent variable set corresponding to the first-level region, spatial distribution prediction layers of the soil physicochemical properties in the optimal independent variable set corresponding to the first-level region are generated according to the layers of the specified environmental variables in Step B.

Step J. The spatial distribution prediction layers of the soil physicochemical properties and the layers of the environmental variables in the optimal independent variable set corresponding to the first-level region are merged, to form an optimal independent variable layer set corresponding to the first-level region. Then, the process proceeds to Step K.

Step K. If R_OLS≥R_NLS, for the sampling sites corresponding to the first-level region, data values of the independent variables are derived from the optimal independent variable layer set, and a linear regression model between the data values of the independent variables in the optimal independent variable set and the data values of the soil dependent variables is trained, to form a first-level region prediction model. Then, the process proceeds to Step L.

If R_NLS>R_OLS, for the sampling sites corresponding to the first-level region, data values of the independent variables are derived from the optimal independent variable layer set corresponding to the first-level region, and a nonlinear regression model between the data values of the independent variables in the optimal independent variable set and the data values of the soil dependent variables is trained, to form a prediction model of the first-level region. Then, the process proceeds to Step L.

Step L. According to the optimal independent variable layer set corresponding to the first-level region, a spatial distribution map of the soil dependent variable, namely, a spatial distribution map of the target soil property in the target region, is generated by applying the first-level region prediction model, to realize prediction of the target soil property in the target region.

Step M. For each second-level region, an optimal independent variable layer set corresponding to the second-level region is acquired by using the method descried in Steps I to J. Then, the process proceeds to Step N.

Step N. If R_OLS_mean≥R_NLS_mean, for each second-level region and for the sampling sites corresponding to the second-level region, data values of independent variables are derived from the optimal independent variable layer set corresponding to the second-level region, and a linear regression model between the data values of the independent variables and the data values of the soil dependent variables is trained, to form a second-level region prediction model, thus obtaining the second-level region prediction model for each of the second-level regions. Then, the process proceeds to Step O.

If R_NLS_mean>R_OLS_mean, for each second-level region and for the sampling sites corresponding to the second-level region, data values of independent variables are derived from the optimal independent variable layer set corresponding to the second-level region, and a nonlinear regression model between the data values of the independent variables and the data value of the soil dependent variable is trained, to form a second-level region prediction model, thus obtaining the second-level region prediction model for each of the second-level regions. Then, the process proceeds to Step O.

Step O. For each second-level region, according to the optimal independent variable layer set corresponding to the second-level region, a spatial distribution map of the soil dependent variable in the second-level region is generated by applying the second-level prediction model, thus obtaining spatial distribution maps of the soil dependent variable in the second-level regions. After combination, a spatial distribution map of the target soil property in the target region is formed, to realize prediction of the target soil property and content in the target region.

The PTF-based method for predicting a target soil property and content designed by the present disclosure is specifically introduced below by using a specific embodiment in which the available copper content in soil in the study sample plot in Xuancheng City, Anhui Province is predicted.

As a prefecture-level city located in the southeast of Anhui Province, Xuancheng is a central city at the intersection of Anhui, Jiangsu and Zhejiang, and is an important channel for the southeast coast to communicate with the mainland. In recent years, the rapid industrial and urban development has led to continuous emission and accumulation of heavy metals, causing serious impacts on grain production and ecological environment. Soil copper is not only involved in the treatment of soil heavy metal pollution, but soil available copper is an essential trace element for crop growth and development. Therefore, technology related to the available copper content in soil has gained great attention all the time.

By the prediction method designed by the present disclosure, the prediction of the available copper in the soil can be realized and available copper data missing from the database can be added; and further, a spatial distribution map of the available copper content in the soil in this region can be produced based on environmental variable layers. As shown in FIG. 1, the following steps are specifically performed:

Step A1. Sampling sites are preset in a target region according to existing soil data in specified data sources, and data values of available copper content, organic matter content, available phosphorus content, available potassium content, available iron content, available manganese content, available zinc content, pH, and total nitrogen content are separately acquired at a soil sample collection depth of 20 cm. Then, the process proceeds to Step A2.

Step A2. Sampling sites of which data values of the corresponding soil physicochemical properties are non-null are selected, and there are 383 sampling sites in this embodiment; and a smallest bounding polygon covering the 383 sampling sites partitions a first-level region, where the sampling sites are used as sampling sites corresponding to the first-level region. Then, the process proceeds to Step A3.

Step A3. The soil dependent variable herein is the available copper content; and the organic matter content, available phosphorus content, available potassium content, available iron content, available manganese content, available zinc content, pH, and total nitrogen content form a soil independent variable set. Then, the process proceeds to Step B.

Following Steps B1 to B5 are performed for implementation of Step B.

Figure 8:
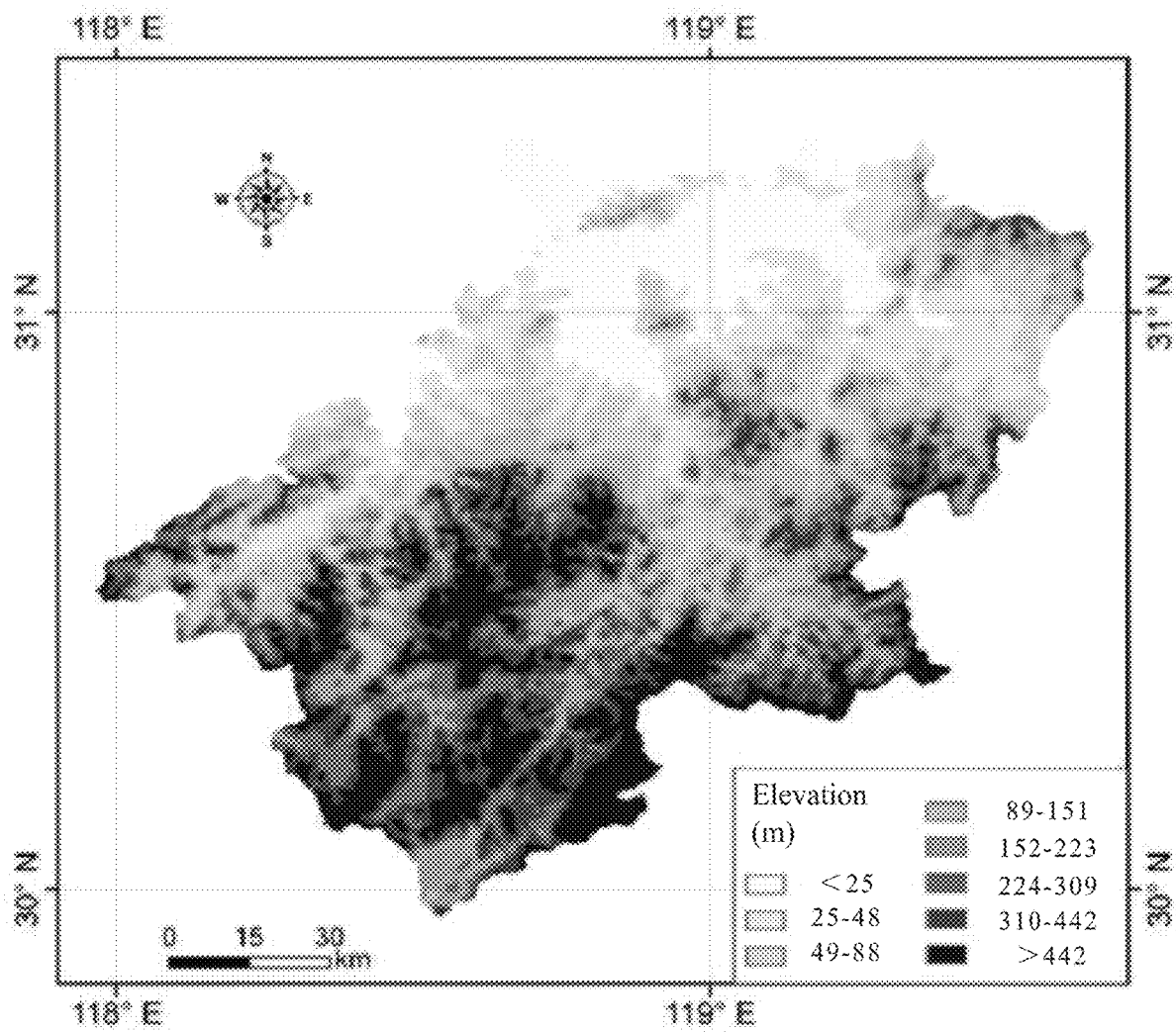
FIG. 8 shows an elevation layer that covers a first-level region in an embodiment of the present disclosure.
Figure 9:
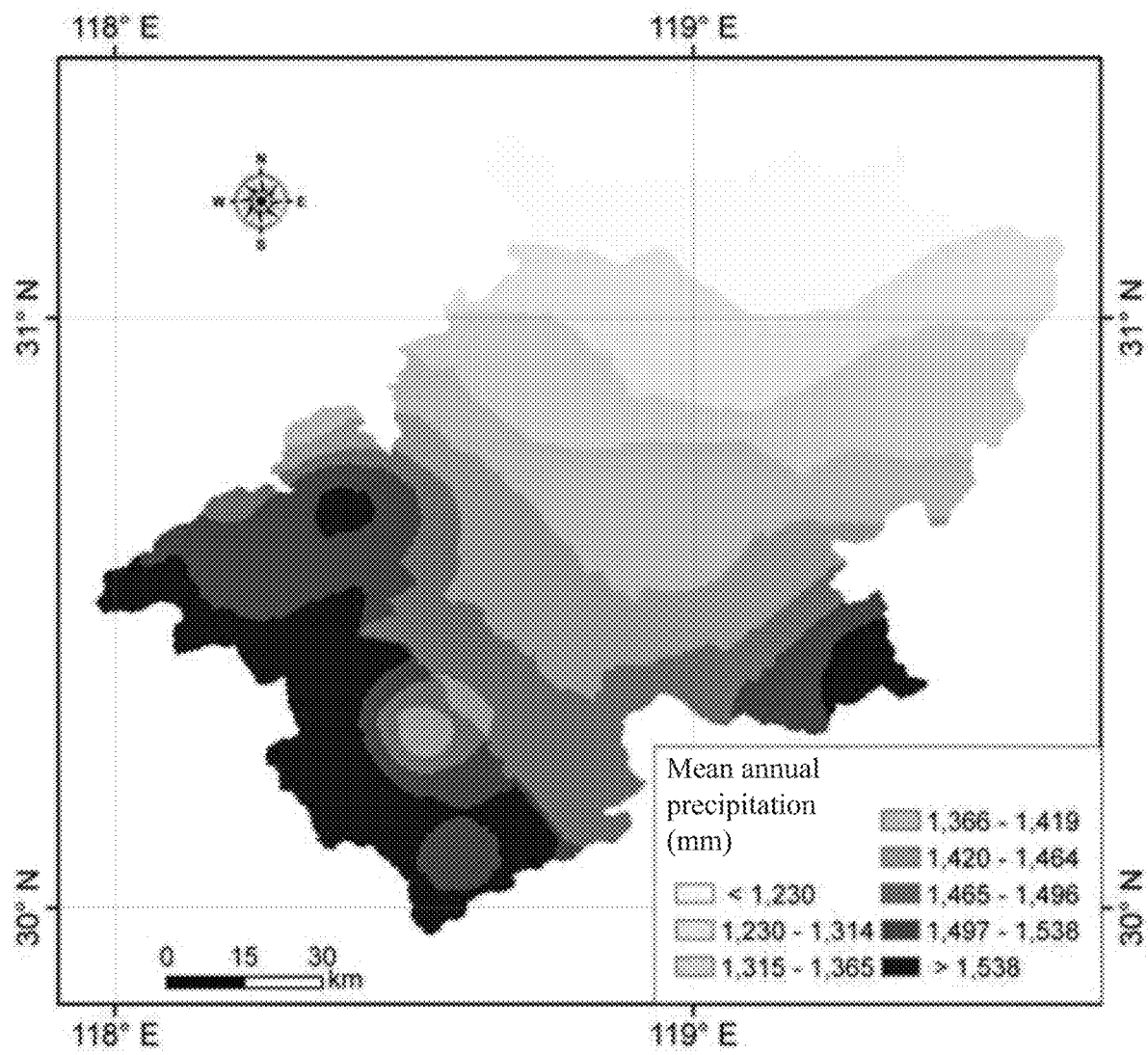
FIG. 9 shows an MAP layer that covers the first-level region in an embodiment of the present disclosure.

Step B1. Layers, covering the first-level region, of specified environmental variables related to the soil dependent variable are acquired, including the elevation (DEM), slope (Slope), profile curvature (ProCur), plane curve (PlanCur), topographic wetness index (TWI), mean annual precipitation (MAP) mean annual temperature (MAT), mean annual soil temperature (SoilTemp), mean annual sunshine (Solar), normalized differential vegetation index (NDVI), and net primary productivity (NPP). For example, an elevation layer that covers the first-level region is shown by FIG. 8, and an MAP layer that covers the first-level region is shown by FIG. 9.

Afterwards, based on the setting of the spatial resolution of 500 m, Steps B2 to B4 are performed, and then Step B5 is performed, to add the specified environmental variables to the soil independent variable set and update the soil independent variable set into {SOM, AP, AK, AFe, AMn, AZn, pH, TN, DEM, Slope, ProCur, PlanCur, TWI, MAP, MAT, SoilTemp, Solar, NDVI, NPP}.

Step C. Independent variables causing multicollinearity, and independent variables of which the correlation with the soil dependent variable, namely, the available copper content, is less than a preset significant difference threshold are deleted from the soil independent variable set, to update the soil independent variable set, where the updated soil independent variable set is {AP, AK, AFe, AZn, pH, TN, DEM, Slope, ProCur, MAP, Solar, NDVI}. Then, the process proceeds to Step D.

Step D is performed according to the foregoing description, to obtain an optimal independent variable set {AZn, pH, TN, DEM, MAP} corresponding to the first-level region. Then, the process proceeds to Step E.

Following Steps E1 to E7 are performed in Step E.

Step E1. A land use layer and a soil-forming parent material layer that cover the first-level region are acquired, and for the sampling sites corresponding to the first-level region, a land use zone and a soil-forming parent material zone where the sampling sites are located are acquired. Then, the process proceeds to Step E2.

Step E2. Based on the data values of the soil dependent variable at the sampling sites corresponding to the first-level region, difference results in the soil dependent variable between the different land use zones and difference results in the soil dependent variable between the different soil-forming parent material zones are analyzed by means of Duncan multiple comparison analysis. Then, the process proceeds to Step E3.

After Steps E1 and E2, the available copper content in the 383 sampling sites in this embodiment can be known through analysis; and there is a difference result greater than the preset significant difference threshold in the difference results in the available copper content between the different soil-forming parent material zones, and none of the difference results in the available copper content between the different land use zones are greater than the preset significant difference threshold.

There are four soil-forming parent materials in total in this region, which are calcareous sedimentary rock and its corresponding metamorphic weathering product, a light-colored crystalline rock weathering product, clastic sedimentary rock and its corresponding metamorphic weathering product, and loess.

Figure 7:
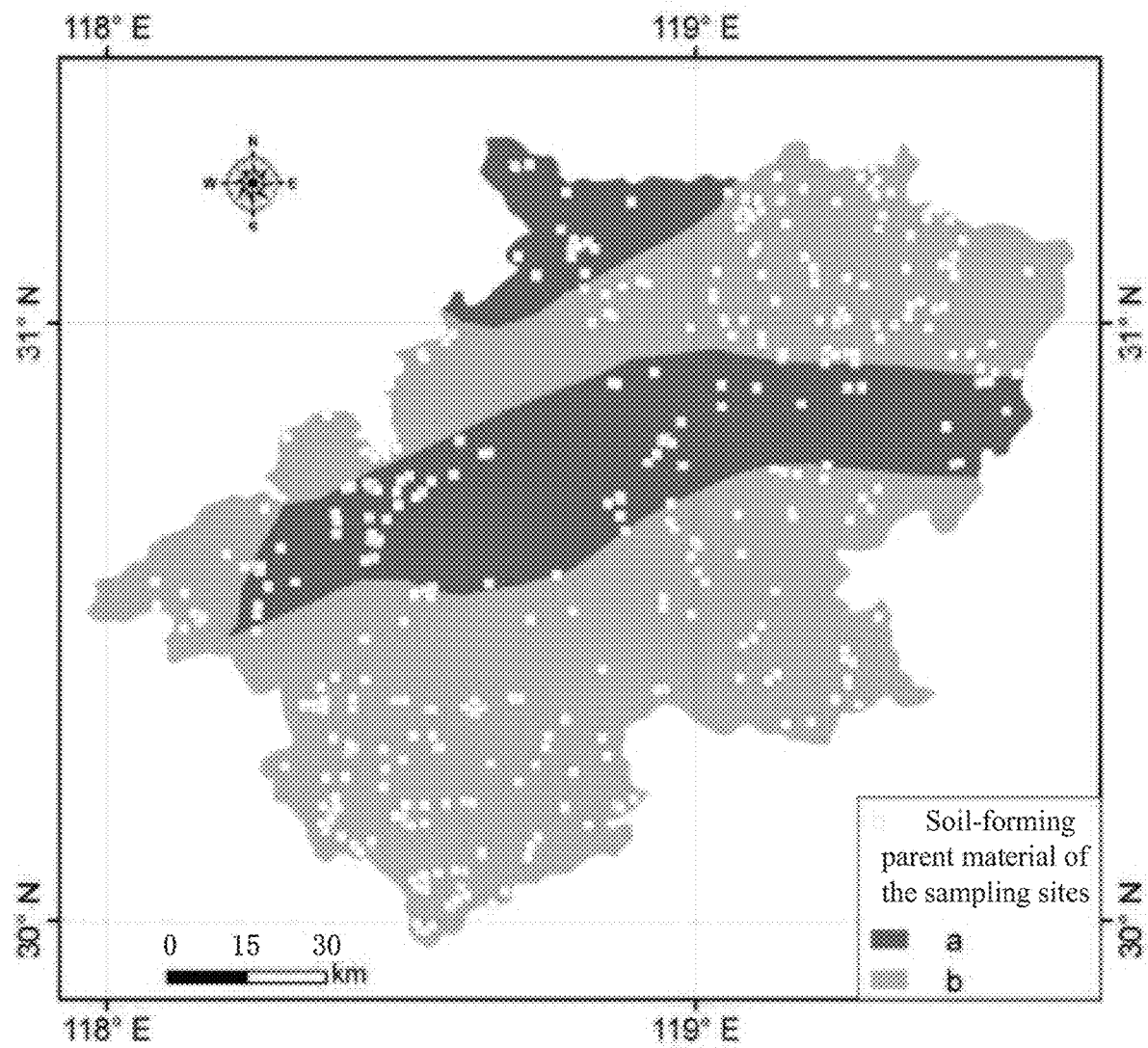
FIG. 7 shows a second-level region layer based on two types of soil-forming parent materials and a spatial distribution of sampling sites in an embodiment of the present disclosure.

Therefore, according to the difference results in the available copper content between the different land use zones, the soil-forming parent material is classified into two types: type a (including the calcareous sedimentary rock and its corresponding metamorphic weathering product) and type b (including the light-colored crystalline rock weathering product, the clastic sedimentary rock and its corresponding metamorphic weathering product, and loess), and a region covering each type of soil-forming parent material after merging is a second-level region. Thus, second-level regions based on the two types of soil-forming parent material are shown by FIG. 7. Then, the process proceeds to Step E7.

Step E7. Spatial overlay is performed for the second-level regions partitioned after merging in the land use layer and the land use zones that are not merged and for the second-level regions partitioned after merging in the soil-forming parent material layer and the soil-forming parent material zones that are not merged, to partition the second-level regions; and sampling sites corresponding to each of the second-level regions are acquired based on the sampling sites corresponding to the first-level region. Then, the process proceeds to Step F.

Step F. For each of the second-level regions, an optimal independent variable set corresponding to each of the second-level region is acquired by using the method described in Step D, and then the process proceeds to Step G.

Following Steps G1 to G10 are performed for implementation of Step G.

Step G1. For the sampling sites corresponding to the first-level region, 75% of the sampling sites are grouped as a training sample and the remaining 25% sampling sites are grouped as a verification sample. Then, the process proceeds to Step G2.

Step G2. For the sampling sites in the training sample, a linear regression model OLS between the data values of the soil dependent variables and the data values of independent variables in the corresponding optimal independent variable set {AZn, pH, TN, DEM, MAP} is trained as follows:

$$ACu=-5.453+0.802 \times AZn+0.615 \times pH+0.712 \times TN-0.00552 \times DEM+0.00232 \times MAP$$

Then, the process proceeds to Step G3.

Then, Steps G3 and G4 are performed to obtain the coefficient R_OLS=0.51 of determination of the linear regression model corresponding to the first-level region, and then the process proceeds to Step G5.

Step G5. For the independent variables in the optimal independent variable set corresponding to the first-level region, fitting of functions, including a power function, an exponential function, a hyperbolic function, and a logarithmic function, is performed for the data values of the soil dependent variables at the sampling sites in the training sample and the data values of the corresponding independent variables. Then, a function with the highest prediction accuracy is selected as a nonlinear fitting manner corresponding to this independent variable, thus obtaining nonlinear fitting manners respectively corresponding to the independent variables in the optimal independent variable set are acquired. Then, the process proceeds to Step G6.

Steps G6 to G8 are further performed successively, to obtain the coefficient R_NLS=0.46 of determination of the nonlinear regression model corresponding to the first-level region. Then, the process proceeds to Step G9.

Step G9. If there is no second-level region, the process directly proceeds to Step H; or if there are second-level regions, the process proceeds to Step G10.

Step G10. For each of the second-level regions, the method described in Steps G1 to G8 is performed, to acquire the coefficients of determination of a linear regression model and a nonlinear regression model corresponding to each of the second-level regions, and to further obtain a mean value R_OLS_mean=0.45 of coefficients of determination of linear regression models corresponding to all the second-level regions and a mean value R_NLS_mean=0.37 of coefficients of determination of nonlinear regression models. Then, the process proceeds to Step H.

After execution of Steps H and H-I, according to R_OLS≥R_NLS, R_OLS≥R_OLS_mean, and R_OLS≥R_NLS_mean, for the sampling sites which lack the data values of the soil dependent variables in the target region, the data values of the soil dependent variables are predicted and added by applying the linear regression model corresponding to the first-level region in Step G. Then, the process proceeds to Step I.

Figure 10:
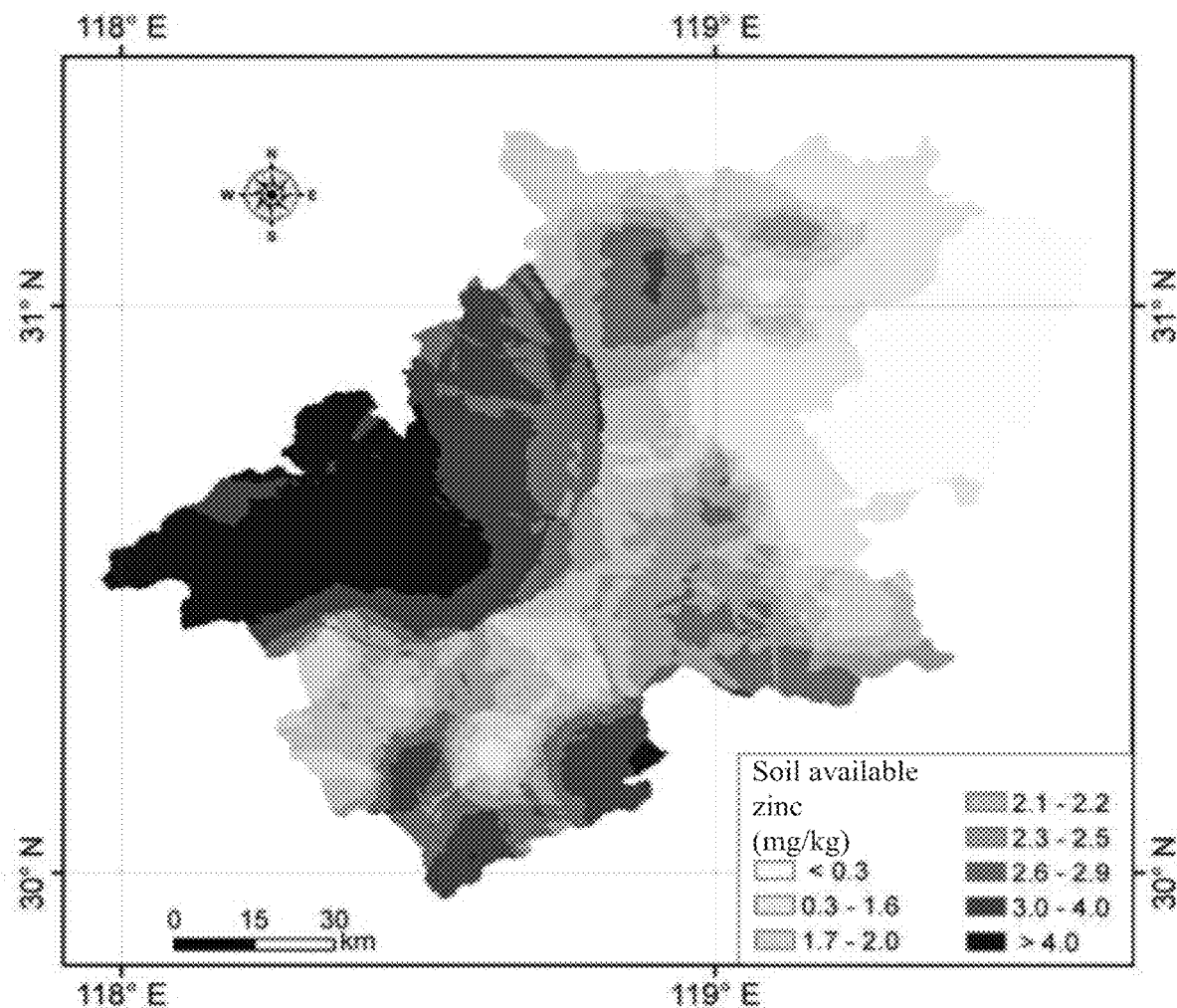
FIG. 10 is a spatial distribution map of an available zinc content in an optimal independent variable set that is produced by prediction in an embodiment of the present disclosure.
Figure 11:
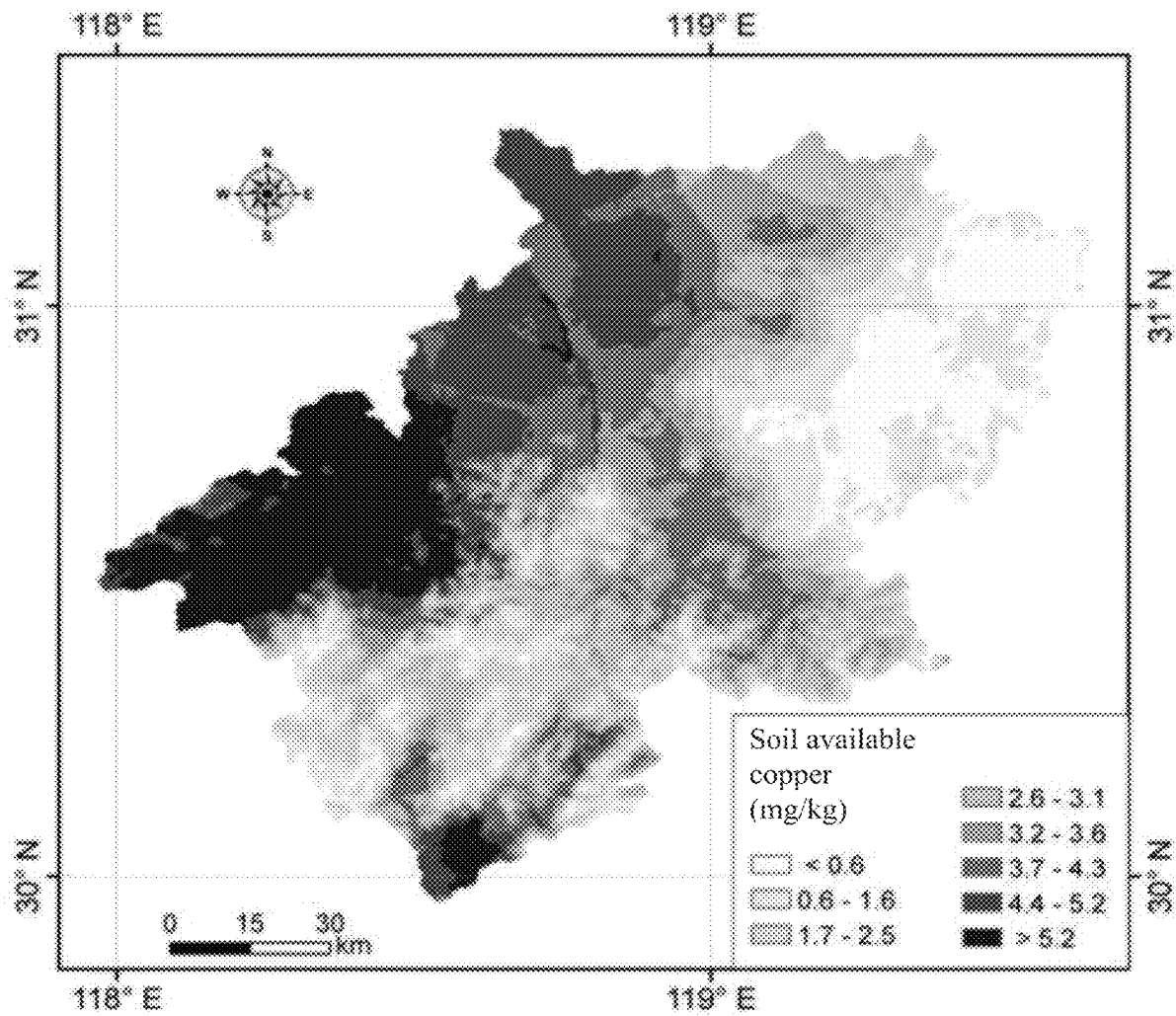
FIG. 11 is a spatial distribution map of a soil dependent variable that is produced by prediction in an embodiment of the present disclosure.

Step I is completed after execution of foregoing Steps I1 and I2, to obtain spatial distribution prediction layers of the soil physicochemical properties in the optimal independent variable set corresponding to the first-level region. For example, a layer of available zinc content that covers the first-level region and is produced by prediction is shown by FIG. 10. Then, proceeds to Step J.

Step J. The spatial distribution prediction layers of the soil physicochemical properties in the optimal independent variable set corresponding to the first-level region and the layers of the environmental variables in the optimal independent variable set corresponding to the first-level region are merged, to form an optimal independent variable layer set corresponding to the first-level region. Then, proceeds to Step K.

Step K. According to R_OLS≥R_NLS, for the sampling sites corresponding to the first-level region, data values of the independent variables are extracted from the optimal independent variable layer set corresponding to the first-level region, and a linear regression model between the data values of the independent variables in the optimal independent variable set and the data values of the soil dependent variables is trained as follows:

$$ACu=-3\ 0.459+1.249 \times AZn+0.939 \times pH+0.127 \times TN-0.00509 \times DEM-0.000522 \times MAP$$

Then, a first-level region prediction model is formed, and proceeds to Step L.

Step L. According to the optimal independent variable layer set corresponding to the first-level region, a spatial distribution map of the soil dependent variable, namely, a spatial distribution map of the available copper content in the target region, is generated by applying the first-level region prediction model, to realize prediction of the target soil property and content in the target region.

In the PTF-based method for predicting a target soil property and content designed by the present disclosure, environmental variables and uncertainty analysis are considered in soil data prediction oriented toward the samplings sites, and the PTF and temporarily produced soil maps are integrated in region-oriented soil map production, thus avoiding uncertainty in prediction of soil data at the sampling sites and production of regional maps, and effectively overcoming the technical bottleneck of a low-precision produced soil map due to low correlation between the environmental variables and the soil physicochemical properties in the conventional digital soil map production method. The method of the present disclosure has good applicability, which can be applied not only in the production of different-scale soil maps of different soil physicochemical properties, but also in the improvement of soil databases of different scales. The proposed technology is to be applied in more technical fields to test its performance.

The embodiments of the present disclosure are described in detail above with reference to the accompanying drawings, but the present disclosure is not limited to the above embodiments. Within the scope of knowledge possessed by those of ordinary skill in the art, various changes can also be made without departing from the purpose of the present disclosure.

What is claimed is:

1. A PTF-based method for predicting a target soil property and content, which is used to predict the target soil property in a target region and comprises following steps:

Step A, selecting, based on existing soil data, sampling sites of which data values of corresponding preset soil physicochemical properties are non-null from the target region, and partitioning a first-level region with a smallest bounding polygon covering all the selected sampling sites, wherein the sampling sites are used as sampling sites corresponding to the first-level region, the preset soil physicochemical properties comprise a target soil property that is referred to as a soil dependent variable and is defined as the target soil property, and rest of the preset soil physicochemical properties that are used to form a soil independent variable set; and then, proceeding to Step B, wherein at least one of the existing soil data is obtained by a field sample collection and a laboratory chemical analysis using at least one technique selected from an atomic absorption spectrometer, a DTPA-TEA extraction method, an atomic absorption spectrophotometer, a high-temperature burning and acid extraction method, a strong acid boiling method, an alkali fusion method, a continuous flow analyzer, and a visible and near infrared reflectance (VNIR) spectra;

Step B, acquiring layers, covering the first-level region, of specified environmental variables related to the soil dependent variable; deriving, for the sampling sites corresponding to the first-level region, values from the specified environmental variables at the sampling sites, and adding the derived values to the soil independent variable set, to update the soil independent variable set; and then, proceeding to Step C;

Step C, deleting independent variables causing multicollinearity and independent variables of which the correlation with the soil dependent variable is less than a preset significant difference threshold, from the soil independent variable set, to update the soil independent variable set; and then, proceeding to Step D;

Step D, training, for the sampling sites corresponding to the first-level region, a linear relationship between the soil dependent variables and the soil independent variables in the soil independent variable set by using a stepwise multiple linear regression model based on a preset number of iterations; separately acquiring a temporary optimal independent variable set during each training iteration, and recording a selection number of each of the temporary optimal independent variable sets; adopting, after completion of training for the preset number of iterations, a temporary optimal independent variable set which is most frequently screened as the optimal independent variable set corresponding to the first-level region; and then, proceeding to Step E;

Step E, acquiring layers of a soil region with preset properties that cover the first-level region, and extracting, for the sampling sites corresponding to the first-level region, soil zones with the preset properties where the sampling sites are located; analyzing and obtaining, based on the data values of the soil dependent variable at the sampling sites, difference results in the soil dependent variable between different soil zones; if none of the difference results are greater than the preset significant difference threshold, proceeding to Step G; merging, if there is a difference result greater than the preset significant difference threshold in the obtained difference results, the soil zones with the difference results not greater than the preset significant difference threshold, and partitioning second-level regions in combination with the soil zones that are not merged; acquiring, based on the sampling sites corresponding to the first-level region, sampling sites corresponding to the second-level regions; and then, proceeding to Step F;

Step F, acquiring, for each of the second-level regions, an optimal independent variable set corresponding to each of the second-level regions by using the method described in Step D, and then proceeding to Step G;

Step G, training, for the sampling sites corresponding to the first-level region, a linear regression model and a nonlinear regression model between the data values of the soil dependent variables and the data values of independent variables in the corresponding optimal independent variable set; and acquiring a coefficient of determination of the linear regression model and that of the nonlinear regression model, wherein the coefficient of determination of the linear regression model corresponding to the first-level region is R1 and the coefficient of determination of the nonlinear regression model corresponding to the first-level region is R2;

further, if there is no second-level region, then, proceeding to Step H; or if there are second-level regions, for the second-level regions, separately training a linear regression model and a nonlinear regression model between the data values of the soil dependent variables at the sampling sites and the data values of the independent variables in the corresponding optimal independent variable set, and acquiring the coefficient of determination of the linear regression model and that of the nonlinear regression model, thus acquiring coefficients of determination of linear regression models and nonlinear regression models corresponding to all the second-level regions, and further acquiring mean values of these coefficients of determination of the linear regression models and nonlinear regression models corresponding to all the second-level regions, which are termed R3 and R4, respectively; and then, proceeding to Step H;

Step H, if there is no second-level region, proceeding to Step I;

if there are second-level regions, when R1 is greater than both R3 and R4 or R2 is greater than both R3 and R4, proceeding to Step I; and when R3 is greater than both R1 and R2 or R4 is greater than both R1 and R2, proceeding to Step M;

Step I, based on the sampling sites corresponding to the first-level region and the corresponding optimal independent variable set, and according to data values of soil physicochemical properties in the optimal independent variable set corresponding to the sampling sites, acquiring a prediction model based on all the specified environmental variables in Step B for the soil physicochemical properties in the optimal independent variable set; acquiring spatial distribution prediction layers of the soil physicochemical properties in the optimal independent variable set corresponding to the first-level region according to the layers of the specified environmental variables in Step B;

and then, proceeding to Step J;

Step J, merging the spatial distribution prediction layers of the soil physicochemical properties and the environmental variables in the optimal independent variable set corresponding to the first-level region, to form an optimal independent variable layer set corresponding to the first-level region; and then, proceeding to Step K;

Step K, if R1≥R2, for the sampling sites corresponding to the first-level region, deriving data values of the independent variables from the optimal independent variable layer set, and training a linear regression model between the data values of the independent variables in the optimal independent variable set and the data values of the soil dependent variables, to form a first-level region prediction model; and then, proceeding to Step L;

if R2>R1, for the sampling sites corresponding to the first-level region, deriving data values of independent variables from the optimal independent variable layer set, and training a nonlinear regression model between the data values of the independent variables in the optimal independent variable set and the data values of the soil dependent variables, to form the first-level region prediction model; and then, proceeding to Step L;

Step L, generating, according to the optimal independent variable layer set corresponding to the first-level region, a spatial distribution map of the soil dependent variable, namely, a spatial distribution map of the target soil property in the target region, by applying the first-level region prediction model, to realize prediction of the target soil property in the target region;

Step M, for each second-level region, acquiring an optimal independent variable layer set corresponding to the each second-level region by using the method descried in Steps I to J; and then, proceeding to Step N;

Step N, if R3≥R4, for each second-level region and for the sampling sites corresponding to the second-level region, deriving data values of independent variables from the optimal independent variable set corresponding to the second-level region, and training a linear regression model between the data values of the independent variables and the data values of the soil dependent variables, to form a second-level region prediction model, thus obtaining the second-level region prediction model for each of the second-level regions; and then, proceeding to Step O;

if R4>R3, for each second-level region and for the sampling sites corresponding to the second-level region, deriving data values of independent variables from the optimal independent variable set corresponding to the second-level region, and training a nonlinear regression model between the data values of the independent variables and the data values of the soil dependent variables, to form the second-level region prediction model, thus obtaining the second-level region prediction model for each of the second-level regions; and then, proceeding to Step O;

Step O, generating, for each second-level region, according to the optimal independent variable layer set corresponding to the second-level region, a spatial distribution map of the soil dependent variable in the second-level region by applying the second-level region prediction model, thus obtaining a spatial distribution map of the soil dependent variable in each of the second-level regions; and obtaining a spatial distribution map of the target soil property in the target region after combination, to predict the target soil property and content in the target region; and Step P, planning a land use of the target region based on the spatial distribution map of the target soil property in the target region.

2. The PTF-based method for predicting the target soil property according to claim 1, further comprising Steps H-I and H-M and Step H, which are as follows:

Step H, if there is no second-level region, proceeding to Step H-I;

if there are second-level regions, when R1 is greater than both R3 and R4 or R2 is greater than both R3 and R4, proceeding to Step H-I; and when R3 is greater than both R1 and R2 or R4 is greater than both R1 and R2, proceeding to Step H-M;

Step H-I, if R1≥R2, for the sampling sites which lack the data values of the soil dependent variables in the target region, predicting and adding the data values of the soil dependent variables by applying the linear regression model corresponding to the first-level region in Step G; and then proceeding to Step I;

if R2>R1, for the sampling sites which lack the data values of the soil dependent variables in the target region, predicting and adding the data values of the soil dependent variables by applying the nonlinear regression model corresponding to the first-level region in Step G; and then proceeding to Step I;

Step H-M, if R3≥R4, for the sampling sites which lack the data values of the soil dependent variables in the target region, predicting and adding the data values of the soil dependent variable by applying the linear regression model corresponding to the second-level regions in Step G; and then proceeding to Step M; and if R4>R3, for the sampling sites which lack the data values of the soil dependent variables in the target region, predicting and adding the data values of the soil dependent variables by applying the nonlinear regression model corresponding to the second-level regions in Step G; and then proceeding to Step M.

3. The PTF-based method for predicting the target soil property and content according to claim 1, wherein Step A comprises the following steps:

Step A1, collecting data values of the preset soil physicochemical properties comprising the target soil property for presetting sampling sites in the target region, according to existing soil data in specified data sources; and then, proceeding to Step A2;

Step A2, selecting the sampling sites of which the data values of the corresponding soil physicochemical properties are non-null, and partitioning a first-level region with a smallest bounding polygon covering all the selected sampling sites, wherein the sampling sites are used as the sampling sites corresponding to the first-level region; and then, proceeding to Step A3; and Step A3, defining the soil dependent variable as the target soil property, and rest of the soil physicochemical properties than the target soil property are used to form a soil independent variable set; and then, proceeding to Step B.

4. The PTF-based method for predicting the target soil property and content according to claim 1, wherein Step B comprises the following steps:

Step B1, acquiring layers, covering the first-level region, of the specified environmental variables related to the soil dependent variable, and then proceeding to Step B2;

Step B2, separately converting the layers of the specified environmental variables to environmental variable grid layers, wherein if the specified environmental variables comprise at least one waveband, each waveband in the specified environmental variables is converted to a corresponding environmental variable grid layer; and then, proceeding to Step B3;

Step B3, resampling for all the environmental variable grid layers by means of bilinear interpolation, and unifying a spatial resolution of grid data to a preset spatial resolution; and then, proceeding to Step B4;

Step B4, acquiring areas corresponding to the first-level region on the environmental variable grid layers, and for the sampling sites corresponding to the first-level region, deriving values from the specified environmental variables at the sampling sites; and then, proceeding to Step B5; and Step B5, adding the derived values to the soil independent variable set, to update the soil independent variable set; and then, proceeding to Step C.

5. The PTF-based method for predicting the target soil property and content according to claim 1, wherein Step C comprises the following steps:

Step C1, for the sampling sites corresponding to the first-level region, training a linear regression model between the soil dependent variables and the independent variables in the soil independent variable set, and acquiring a coefficient $R_k^2$ of determination of the independent variables in the soil independent variable set, wherein $R_k^2$ denotes a coefficient of determination of the $k^{th}$ independent variable in the soil independent variable set; and then, proceeding to Step C2;

Step C2, for the independent variables in the soil independent variable set, acquiring a coefficient of variance expansion of the independent variables according to a calculation result of $$\frac{1}{1-R_k^2};$$

and then, proceeding to Step C3;

Step C3, determining whether the coefficients of variance expansion of the independent variables in the soil independent variable set are all less than a preset coefficient threshold, and proceeding to Step C4 if yes; or otherwise, deleting an independent variable with the largest coefficient of variance expansion from the soil independent variable set to update the soil independent variable set, and returning to Step C1; and Step C4, for the sampling sites corresponding to the first-level region, calculating the correlations between the data values of the soil dependent variables and the data values of the independent variables in the soil independent variable set, and deleting the independent variables of which the correlation is less than the preset significant difference threshold from the soil independent variable set, to update the soil independent variable set; and then, proceeding to Step D.

6. The PTF-based method for predicting the target soil property and content according to claim 1, wherein in Step D, after completion of training for the preset number of iterations, the temporary optimal independent variable set which is most frequently screened is adopted as a candidate optimal independent variable set corresponding to the first-level region; and Step D further comprises the following steps:

Step D1, for the sampling sites corresponding to the first-level region, continuously training a linear relationship between the soil dependent variables and the soil independent variables in the soil independent variable set by using the stepwise multiple linear regression model and based on a preset number of incremental iterations; separately acquiring a temporary optimal independent variable set during each iterative training, and continuously recording the selection number of each of the temporary optimal independent variable sets; after completion of training for the preset number of iterations, adopting the temporary optimal independent variable set which is mostly frequently screened as a candidate optimal independent variable set corresponding to the first-level region; and then, proceeding to Step D2; and Step D2, determining whether the two latest obtained candidate optimal independent variable sets corresponding to the first-level region are consistent, and if yes, adopting the candidate optimal independent variable set as the optimal independent variable set corresponding to the first-level region, and proceeding to Step E; or otherwise, returning to Step D1.

7. The PTF-based method for predicting the target soil property and content according to claim 1, wherein Step E comprises the following steps:

Step E1, acquiring a land use layer and a soil-forming parent material layer that cover the first-level region, and for the sampling sites corresponding to the first-level region, extracting a land use zone and a soil-forming parent material zone where the sampling sites are located; and then, proceeding to Step E2;

Step E2, analyzing and obtaining, based on the data values of the soil dependent variable at the sampling sites corresponding to the first-level region, difference results in the soil dependent variable between the different land use zones and difference results in the soil dependent variable between the different soil-forming parent material zones by means of Duncan multiple comparison analysis; and then, proceeding to Step E3;

Step E3, if none of the difference results in the soil dependent variable between the different land use zones and the difference results in the soil dependent variable between the different soil-forming parent material zones are greater than a preset significant difference threshold, proceeding to Step G; or otherwise, proceeding to Step E4;

Step E4, if there is a difference result greater than the preset significant difference threshold in the difference results in the soil dependent variable between the different land use zones, and none of the difference results in the soil dependent variable between the different soil-forming parent material zones are greater than the preset significant difference threshold, merging the different land use zones with the difference results not greater than the preset significant difference threshold to partition the second-level regions; and then, proceeding to Step E7; or otherwise, proceeding to Step E5;

Step E5, if there is a difference result greater than the preset significant difference threshold in the difference results in the soil dependent variable between the different soil-forming parent material zones, and none of the difference results in the soil dependent variable between the different land use zones are greater than the preset significant difference threshold, merging the different soil-forming parent material zones with the difference results not greater than the preset significant difference threshold to partition the second-level regions; and then, proceeding to Step E7; or otherwise, proceeding to Step E6;

Step E6, if there is a difference result greater than the preset significant difference threshold in both the difference results in the soil dependent variable between the different soil-forming parent material zones and the difference results in the soil dependent variable between the different land use zones, merging the different soil-forming parent material zones with the difference results not greater than the preset significant difference threshold to partition the second-level regions, and merging the different land use zones with the difference results not greater than the preset significant difference threshold to partition the second-level regions; and then, proceeding to Step E7; and Step E7, partitioning the second-level regions by performing spatial overlay for the second-level regions partitioned after merging in the land use layer and the land use zones that are not merged and for the second-level regions partitioned after merging in the soil-forming parent material layer and the soil-forming parent material zones that are not merged; and acquiring the sampling sites corresponding to each of the second-level regions based on the sampling sites corresponding to the first-level region; and then, proceeding to Step F.

8. The PTF-based method for predicting the target soil property and content according to claim 1, wherein Step G comprises the following steps:

Step G1, among the sampling sites corresponding to the first-level region, grouping the sampling sites with a first preset proportion as a training sample and grouping the sampling sites remained as a verification sample, wherein the first preset proportion is greater than 50%; and then, proceeding to Step G2;

Step G2, for the sampling sites in the training sample, training a linear regression model between the data values of the soil dependent variables and the data values of independent variables in the corresponding optimal independent variable set, and then, proceeding to Step G3;

Step G3, for data values of independent variables in the optimal independent variable set corresponding to the sampling sites in the verification sample, obtaining predicted data values of the soil dependent variables at the sampling sites in the verification sample by applying the linear regression model; and then proceeding to Step G4;

Step G4, calculating, for the sampling sites in the verification sample, a coefficient of determination between the data values of the soil dependent variables and the corresponding predicted data values of the soil dependent variables, which is termed R1 of the linear regression model corresponding to the first-level region; and then proceeding to Step G5;

Step G5, for the independent variables in the optimal independent variable set corresponding to the first-level region, performing fitting of preset specified functions for the data values of the soil dependent variables at the sampling sites in the training sample and the data values of the corresponding independent variables; selecting a function with the highest prediction accuracy as a nonlinear fitting manner corresponding to the independent variable, thus obtaining nonlinear fitting manners respectively corresponding to the independent variables in the optimal independent variable set; and then, proceeding to Step G6;

Step G6, according to the nonlinear fitting manners respectively corresponding to the independent variables in the optimal independent variable set corresponding to the first-level region, for the sampling sites in the training sample, training a nonlinear regression model between the data values of the soil dependent variables and the data values of the independent variables in the corresponding optimal independent variable set by using the nonlinear least square method; and then, proceeding to Step G7;

Step G7, for the data values of independent variables in the optimal independent variable set corresponding to the sampling sites in the verification sample, obtaining predicted data values of the soil dependent variables at the sampling sites in the verification sample by applying the nonlinear regression model NLS; and then proceeding to Step G8;

Step G8, calculating, for the sampling sites in the verification sample, a coefficient of determination between the data values of the soil dependent variables and the predicted data value of the soil dependent variable, which is termed R2 of the nonlinear regression model corresponding to the first-level region; and then proceeding to Step G9;

Step G9, if there is no second-level region, proceeding to Step H directly; or if there are second-level regions, proceeding to Step G10; and Step G10, Performing, for all the second-level regions, Steps G1 to G8, to acquire the coefficients of determination of linear regression models and nonlinear regression models corresponding to all the second-level regions and to further acquire the mean values of these coefficients of determination of linear regression models and nonlinear regression models corresponding to all the second-level regions, which are termed R3 and R4, respectively, and then, proceeding to Step H.

9. The PTF-based method for predicting the target soil property and content according to claim 1, wherein Step I comprises the following steps:

Step I1, based on the sampling sites corresponding to the first-level region and the corresponding optimal independent variable set, for the soil physicochemical properties in the optimal independent variable set, separately training specified prediction models by means of 10-fold cross-validation according to the data values of the soil physicochemical properties corresponding to the sampling sites and the data values of the specified environmental variables in Step B, to obtain different prediction models; selecting a prediction model with the highest prediction accuracy as a prediction model based on all the specified environmental variables in Step B for the soil physicochemical property, thus obtaining prediction models based on all the specified environmental variables in Step B for the different soil physicochemical properties in the optimal independent variable set; and then, proceeding to Step I2; and Step I2, according to the prediction model based on all the specified environmental variables in Step B for the soil physicochemical properties in the optimal independent variable set corresponding to the first-level region with each the layers of specified environmental variables in Step B, generating spatial distribution prediction layers of the soil physicochemical properties in the optimal independent variable set corresponding to the first-level region according to the layers of the specified environmental variables in Step B.

10. The PTF-based method for predicting the target soil property and content according to claim 1, wherein in Step P, the land use comprises conducting a pollution prevention treatment or a farmland development.

\* \* \* \* \*